United States Patent
Ishikawa

(10) Patent No.: US 10,238,414 B2
(45) Date of Patent: Mar. 26, 2019

(54) JOINT SURGICAL SYSTEM

(71) Applicant: OLYMPUS CORPORATION, Hachioji-shi, Tokyo (JP)

(72) Inventor: Manabu Ishikawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 9 days.

(21) Appl. No.: 15/366,312

(22) Filed: Dec. 1, 2016

(65) Prior Publication Data
US 2017/0079678 A1 Mar. 23, 2017

Related U.S. Application Data

(63) Continuation of application No. PCT/JP2016/052303, filed on Jan. 27, 2016.

(30) Foreign Application Priority Data

Feb. 18, 2015 (JP) ................................. 2015-029836

(51) Int. Cl.
*A61B 18/12* (2006.01)
*A61B 17/32* (2006.01)
(Continued)

(52) U.S. Cl.
CPC ...... *A61B 17/320068* (2013.01); *A61B 1/317* (2013.01); *A61B 17/320016* (2013.01);
(Continued)

(58) Field of Classification Search
CPC .. A61B 17/320068; A61B 2018/00714; A61B 2018/00791–2018/00821; A61B 2018/00982; A61B 2018/00994
(Continued)

(56) References Cited

U.S. PATENT DOCUMENTS

2003/0208193 A1* 11/2003 Van Wyk ........... A61B 18/1206
606/34
2008/0058845 A1* 3/2008 Shimizu ................ A61B 17/29
606/169
(Continued)

FOREIGN PATENT DOCUMENTS

CN 102665585 A 9/2012
JP H03-131245 A 6/1991
(Continued)

OTHER PUBLICATIONS

Aug. 22, 2017 International Preliminary Report on Patentability issued in International Application No. PCT/JP2016/052303.
(Continued)

*Primary Examiner* — Daniel W Fowler
*Assistant Examiner* — Sean W Collins
(74) *Attorney, Agent, or Firm* — Oliff PLC

(57) ABSTRACT

A joint surgical system includes, a treatment tool, a high-frequency output section which outputs high-frequency energy to the treatment tool, an ultrasonic output section which outputs ultrasonic energy to the treatment tool, a measurement section which measures a temperature of the liquid, and a control section which controls the high-frequency output section to stop output of the high-frequency energy and controls the ultrasonic output section to continue output of the ultrasonic energy when a measurement temperature measured by the measurement section is equal to or higher than a predetermined temperature.

11 Claims, 13 Drawing Sheets

(51) Int. Cl.
   *A61B 1/317*   (2006.01)
   *A61B 18/14*   (2006.01)
   *A61B 1/00*    (2006.01)
   *A61B 17/00*   (2006.01)
   *A61B 18/00*   (2006.01)
   *A61B 90/00*   (2016.01)

(52) U.S. Cl.
   CPC ........ *A61B 18/148* (2013.01); *A61B 1/00045* (2013.01); *A61B 90/37* (2016.02); *A61B 2017/00084* (2013.01); *A61B 2017/00115* (2013.01); *A61B 2017/320084* (2013.01); *A61B 2018/00672* (2013.01); *A61B 2018/00678* (2013.01); *A61B 2018/00791* (2013.01); *A61B 2018/00982* (2013.01); *A61B 2018/00994* (2013.01); *A61B 2018/1472* (2013.01); *A61B 2217/007* (2013.01)

(58) Field of Classification Search
   USPC ........................................................ 606/169
   See application file for complete search history.

(56) References Cited

U.S. PATENT DOCUMENTS

| | | | | |
|---|---|---|---|---|
| 2009/0254080 | A1* | 10/2009 | Honda | A61B 18/1402 606/38 |
| 2010/0179546 | A1* | 7/2010 | Cunningham | A61B 18/1442 606/51 |
| 2010/0191173 | A1* | 7/2010 | Kimura | A61B 17/32006 604/21 |
| 2011/0087212 | A1* | 4/2011 | Aldridge | A61B 17/32009 606/34 |
| 2011/0270242 | A1* | 11/2011 | Marion | A61B 18/148 606/35 |
| 2013/0116689 | A1* | 5/2013 | Marion | A61B 5/01 606/42 |
| 2014/0012297 | A1* | 1/2014 | Ross | A61B 17/32009 606/169 |

FOREIGN PATENT DOCUMENTS

| | | |
|---|---|---|
| JP | H06-502573 A | 3/1994 |
| JP | 2000-217835 A | 8/2000 |
| JP | 2001-511043 A | 8/2001 |
| JP | 2001-314411 A | 11/2001 |
| JP | 2003-135481 A | 5/2003 |
| JP | 2010-005370 A | 1/2010 |
| KR | 2013-0136809 A | 12/2013 |
| WO | 2010/087060 A1 | 8/2010 |

OTHER PUBLICATIONS

Apr. 26, 2016 International Search Report issued in International Patent Application No. PCT/JP2016/052303.

Jun. 4, 2018 Office Action issued in Chinese Application No. 201680001481.5.

Sep. 27, 2018 Extended European Search Report issued in European Application No. 16752224.2.

Dec. 21, 2018 Office Action issued in Chinese Application No. 201680001481.5.

* cited by examiner

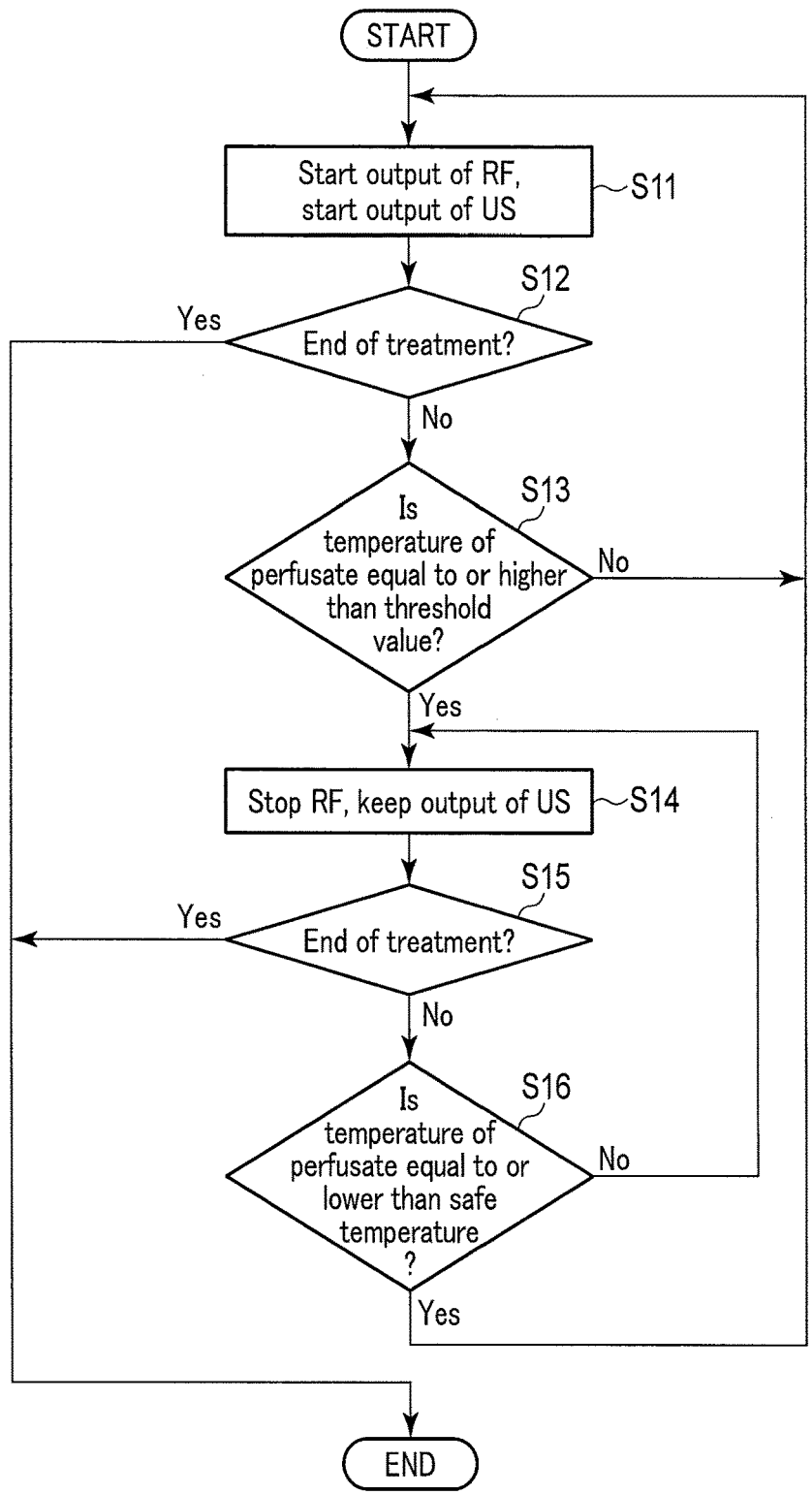
F I G. 3

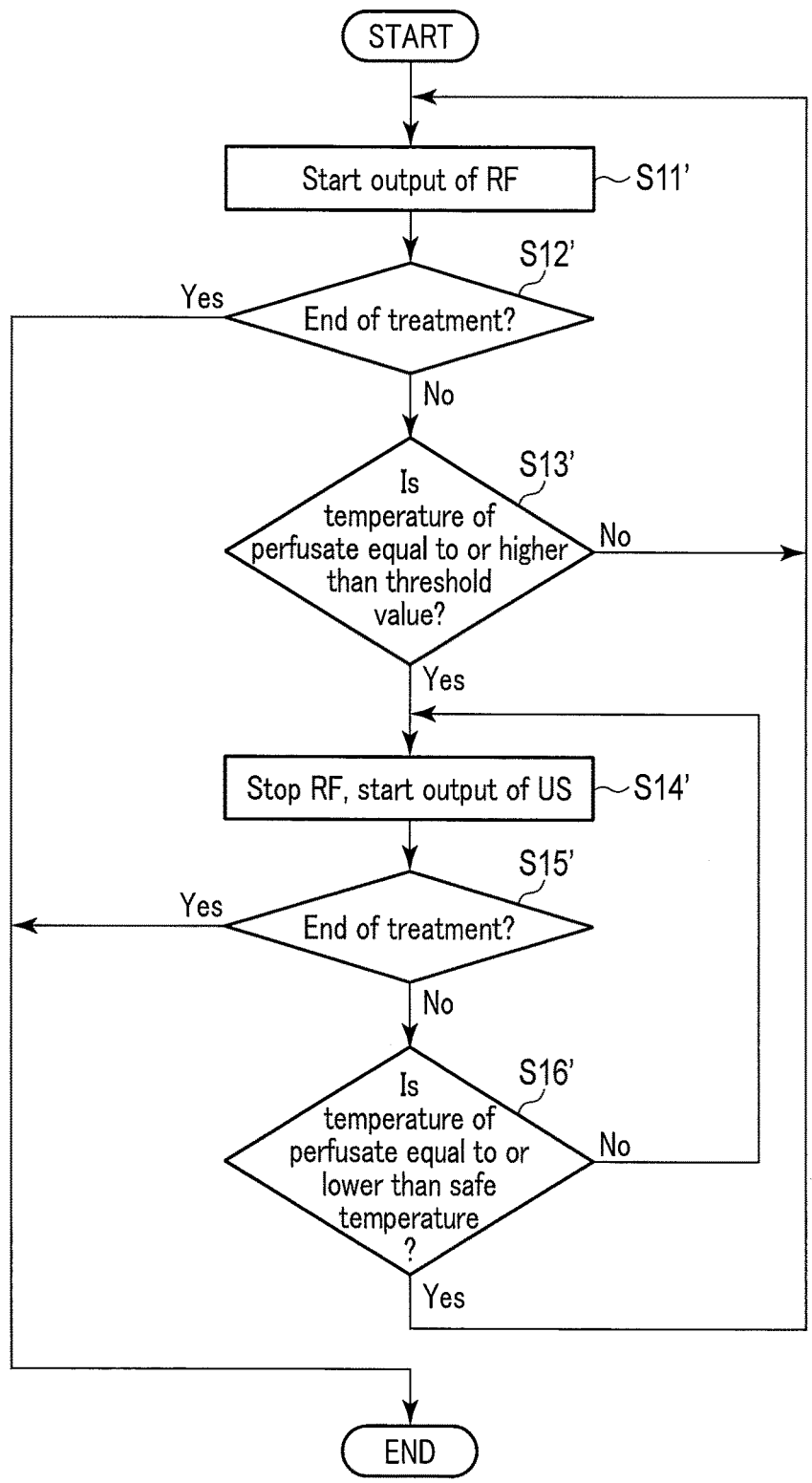
F I G. 4

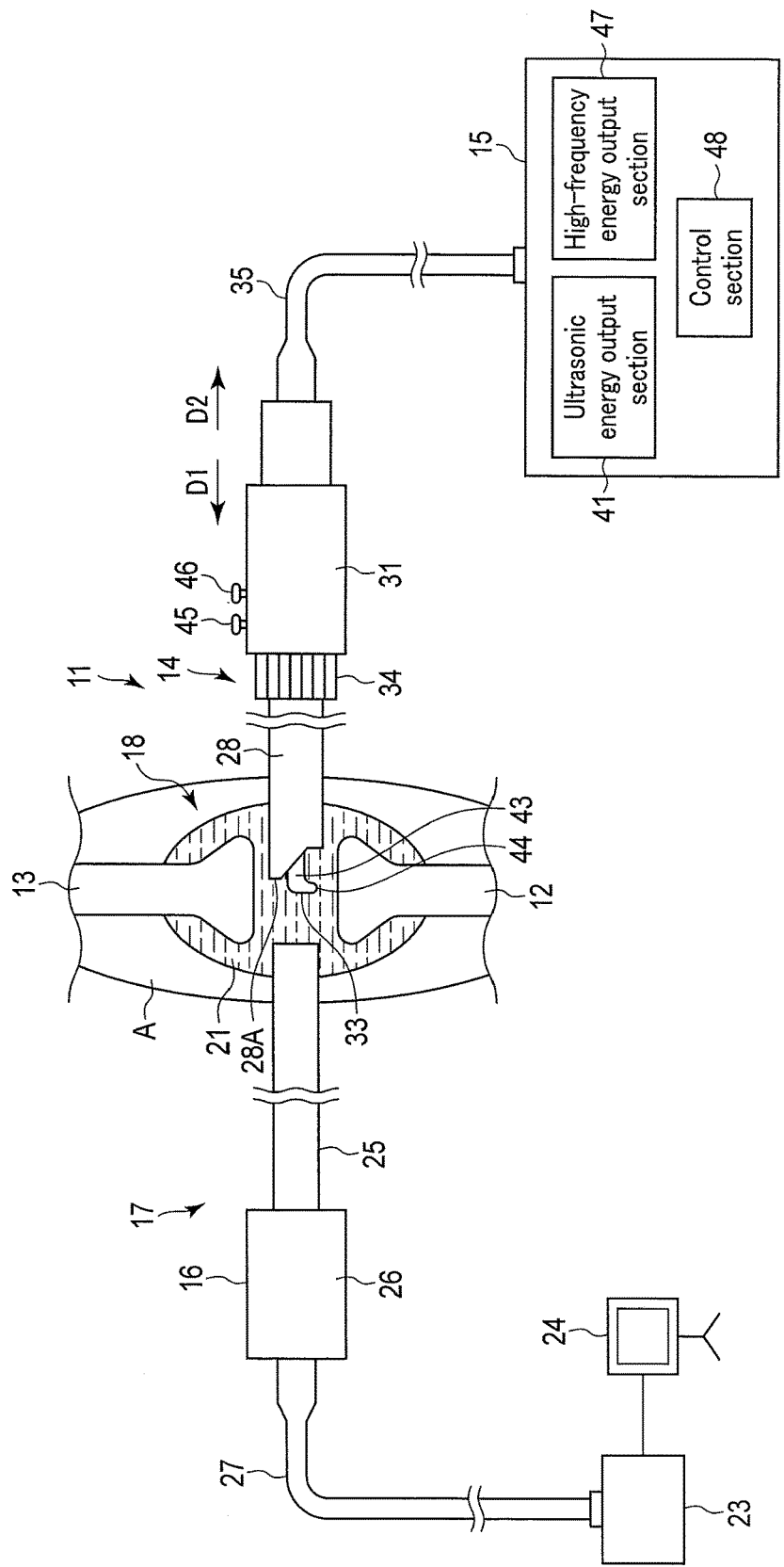
F I G. 5

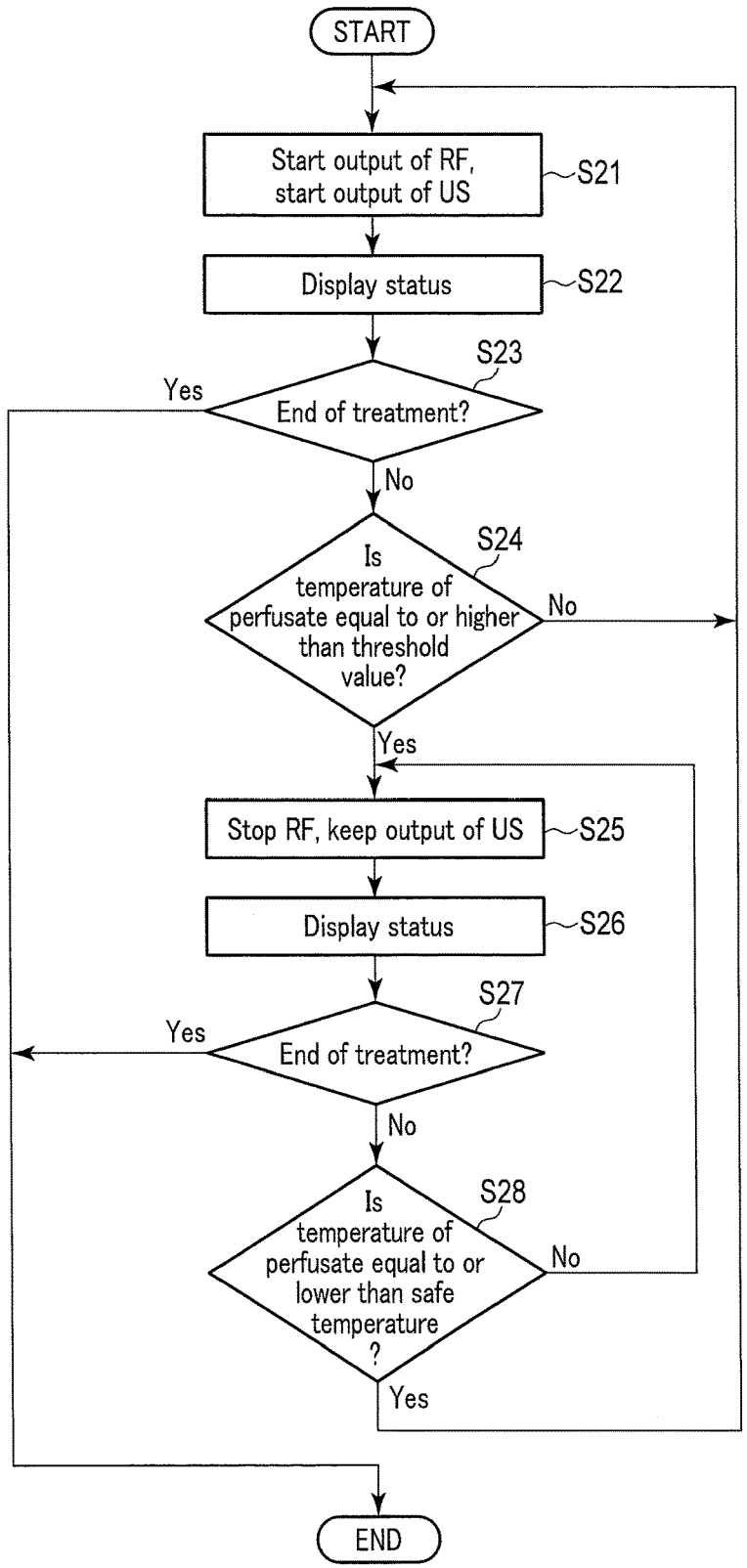
F I G. 7

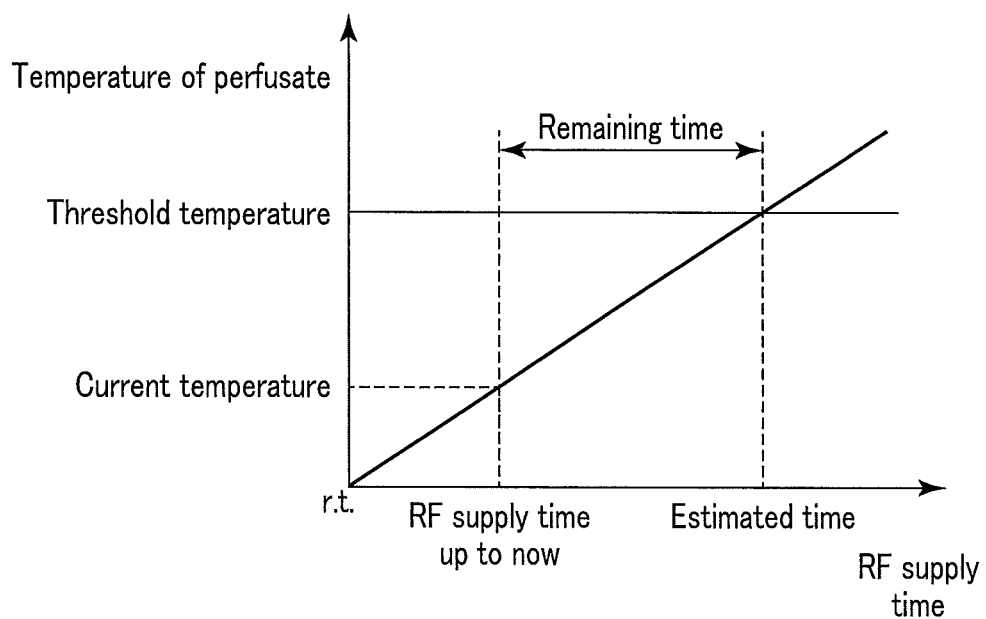
F I G. 10

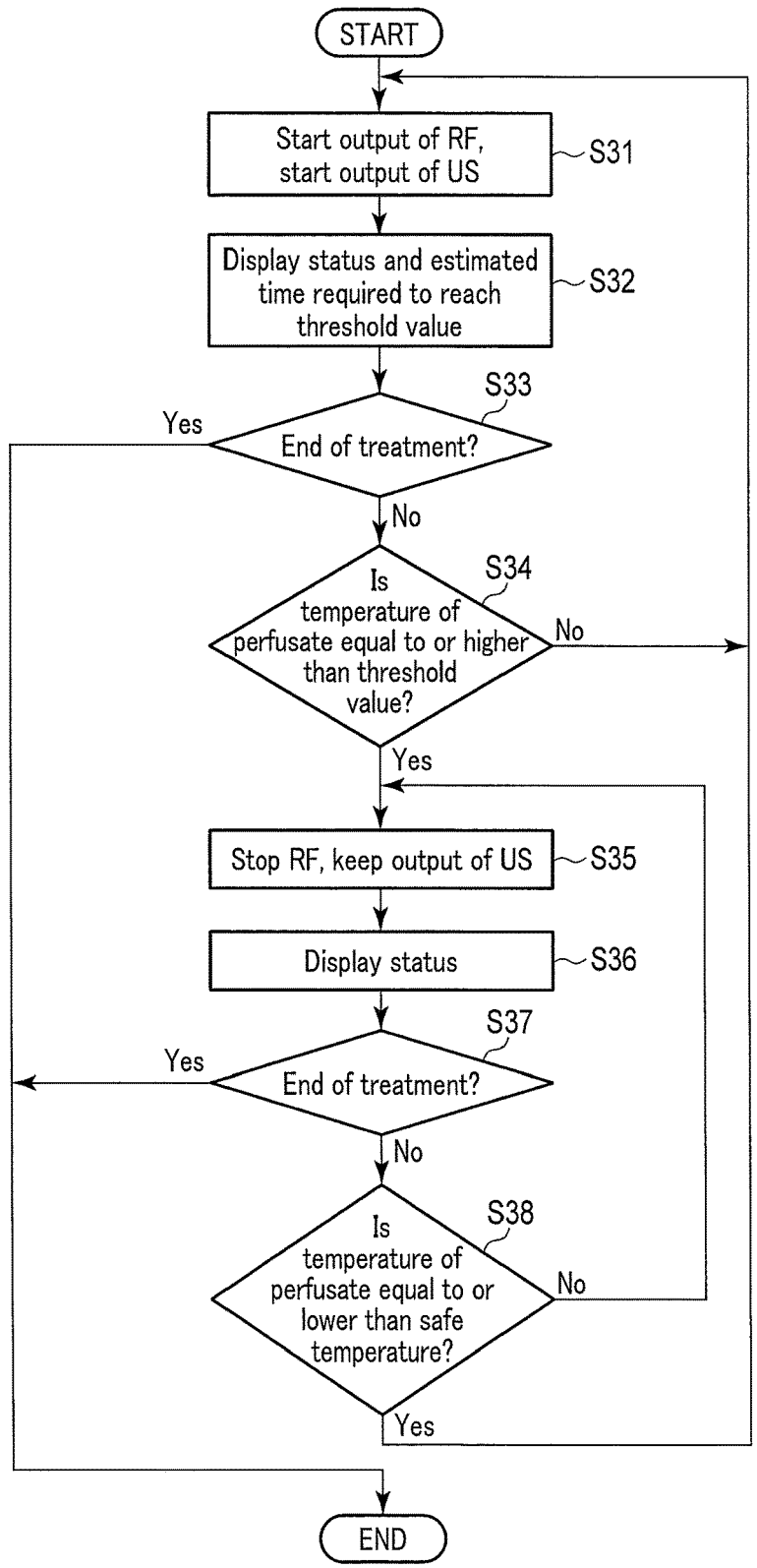
F I G. 11

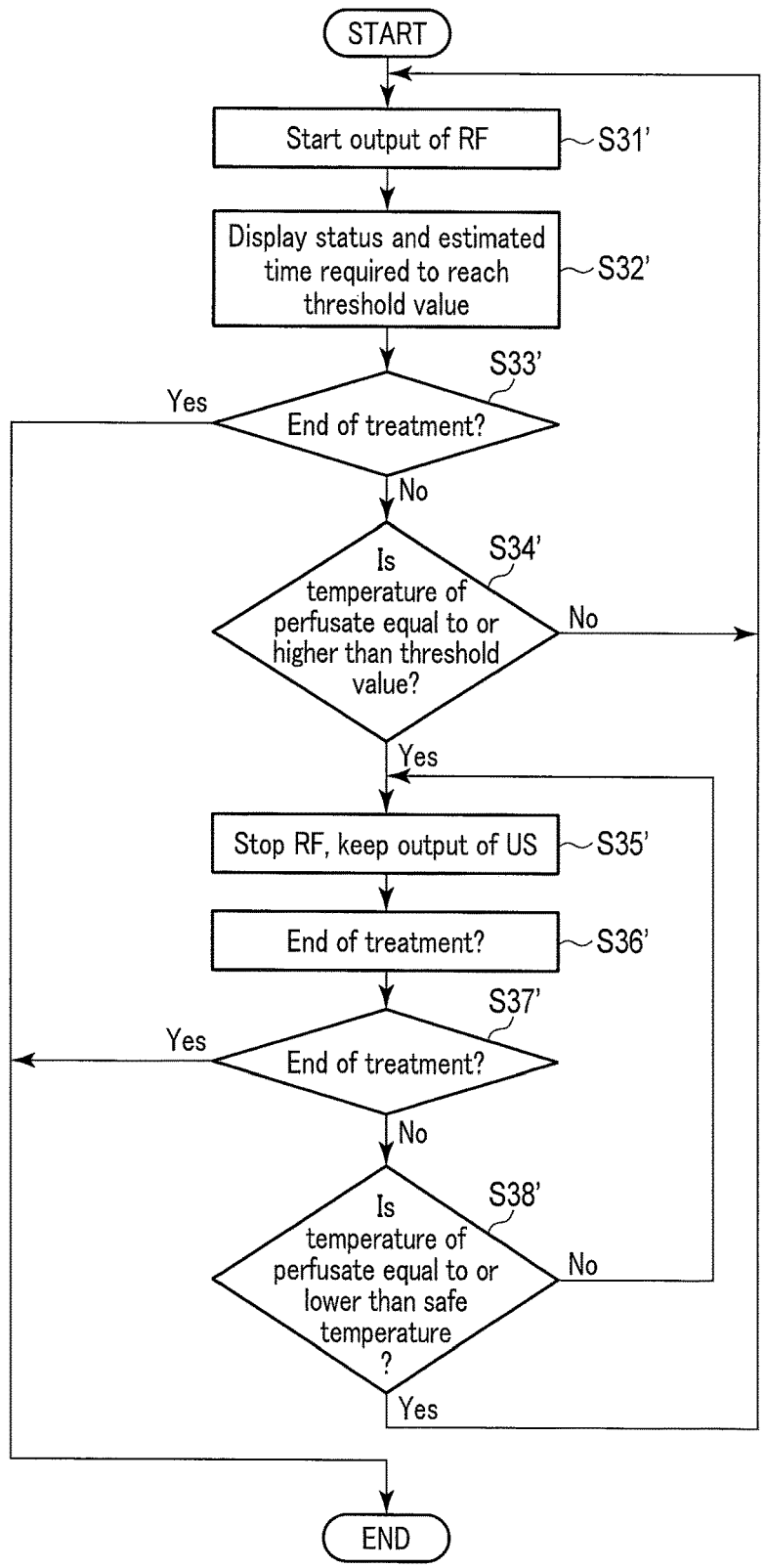
F I G. 12

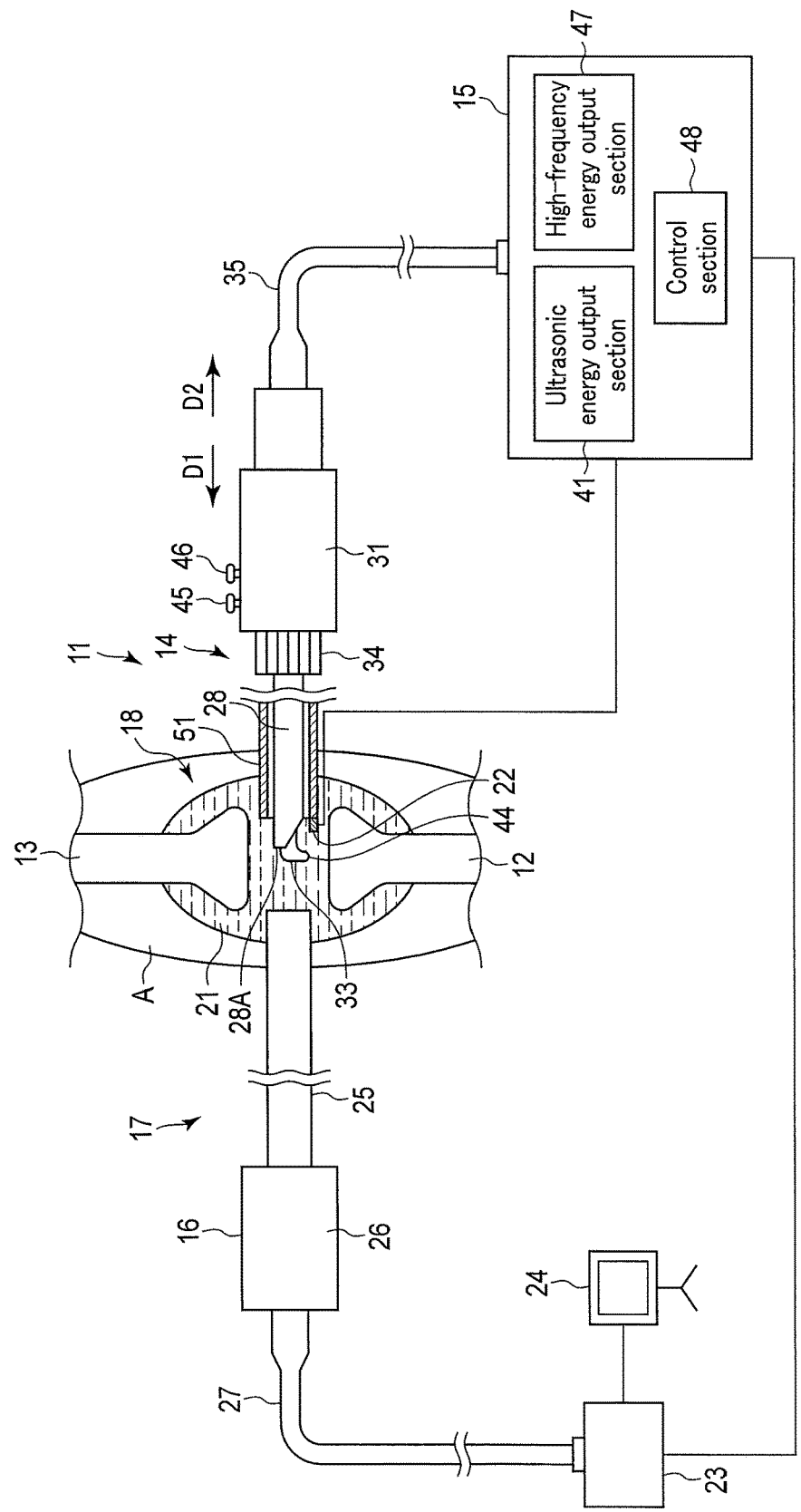
F I G. 13

JOINT SURGICAL SYSTEM

CROSS-REFERENCE TO RELATED APPLICATIONS

This application is a Continuation Application of PCT Application No. PCT/JP2016/052303, filed Jan. 27, 2016 and based upon and claiming the benefit of priority from prior Japanese Patent Application No. 2015-029836, filed Feb. 18, 2015, the entire contents of all of which are incorporated herein by reference.

BACKGROUND OF THE INVENTION

1. Field of the Invention

The present invention relates to a joint surgical system which can be used in arthroscopic surgery.

2. Description of the Related Art

In arthroscopic surgery in an orthopedic field, a treatment is given while swelling a joint cavity with a liquid (a perfusate) such as a normal saline solution to assure an operative field. A treatment tool used in such arthroscopic surgery is disclosed in, e.g., Jpn. PCT National Publication No. 2001-511043. The treatment tool disclosed in this reference includes a mechanical cutting section using a rotary blade or a bar and an electronic cutting and cautery section using a high-frequency current. In this reference, one treatment tool enables multiple treatments.

BRIEF SUMMARY OF THE INVENTION

Meanwhile, in the arthroscopic surgery, a treatment is performed in the above-described liquid. Thus, in the treatment tool in Jpn. PCT National Publication No. 2001-511043, when a high-frequency current is used to keep giving the treatment, an inconvenience which is an increase in temperature of the liquid arises.

It is an object of the present invention to provide a joint surgical system which can prevent a thermal burn to surrounding tissues and efficiently give a treatment to a treatment target region.

A joint surgical system comprising, a treatment tool configured to give a high-frequency treatment using a high-frequency current and an ultrasonic treatment using ultrasonic vibration to a treatment target region in a joint cavity filled with a liquid having electrical conductivity, a high-frequency output section which outputs high-frequency energy for the high-frequency treatment to the treatment tool, an ultrasonic output section which outputs ultrasonic energy for the ultrasonic treatment to the treatment tool, a measurement section which measures a temperature of the liquid, and a control section which controls the high-frequency output section to stop output of the high-frequency energy and controls the ultrasonic output section to continue output of the ultrasonic energy when a measurement temperature measured by the measurement section is equal to or higher than a predetermined temperature.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 is a flowchart showing a procedure of an incision or excision treatment using the joint surgical system depicted in FIG. 1;

FIG. 4 is a flowchart showing a procedure of a hemostatic treatment using the joint surgical system depicted in FIG. 1;

FIG. 5 is a schematic view showing a modification of a joint surgical system according to a modification of the first embodiment;

FIG. 7 is a flowchart showing a procedure of an incision or excision treatment using the joint surgical system depicted in FIG. 6;

FIG. 10 is a graph schematically showing an estimated time calculation method executed by a control section in a joint surgical system according to a third embodiment;

FIG. 11 is a flowchart showing a procedure of an incision or excision treatment using the joint surgical system according to the third embodiment;

FIG. 12 is a flowchart showing a procedure of a hemostatic treatment using the joint surgical system according to the third embodiment; and FIG. 13 is a schematic view showing a joint surgical system according to a fourth embodiment.

DETAILED DESCRIPTION

First Embodiment

Figure 1:
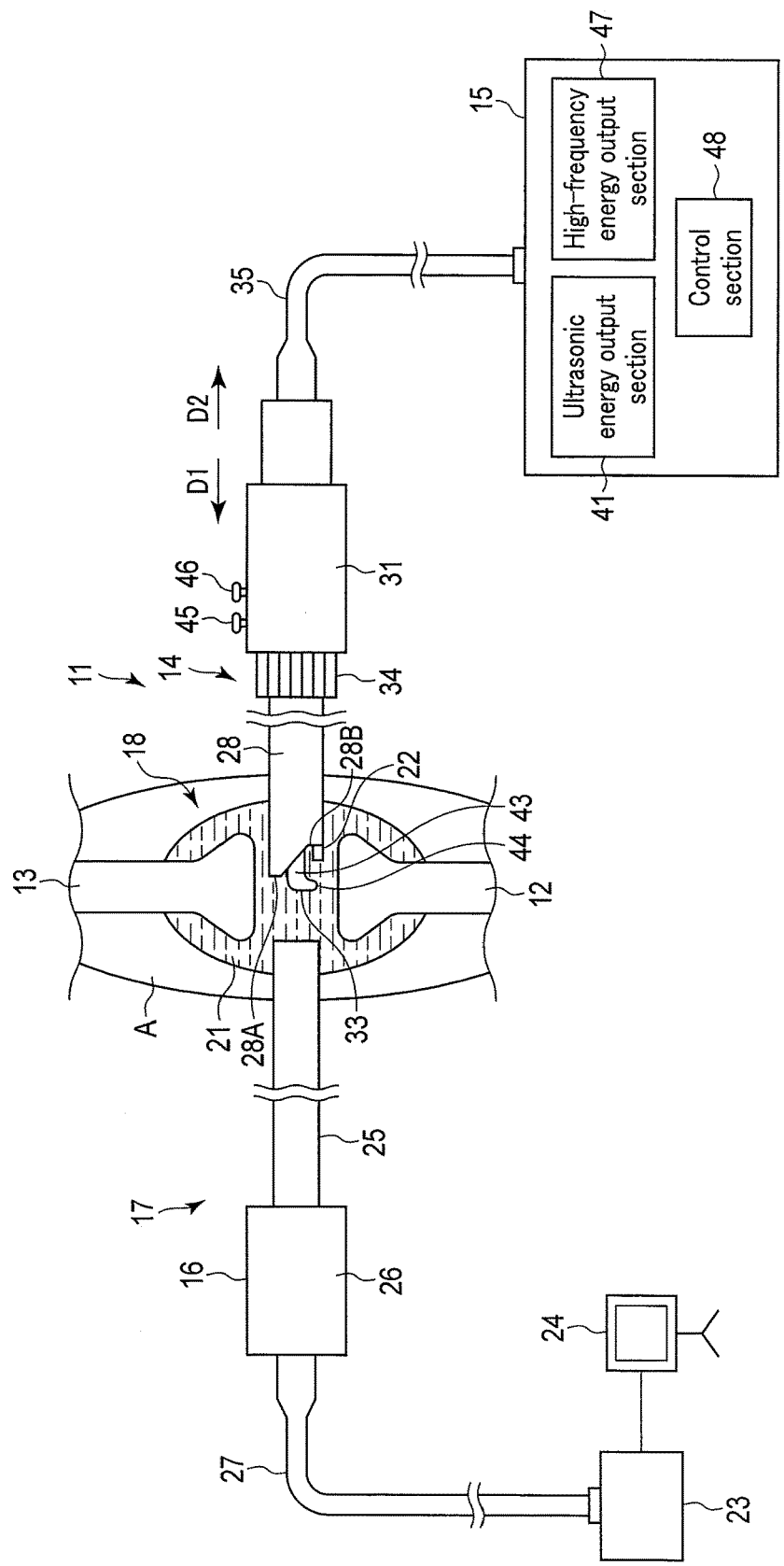
FIG. 1 is a schematic view showing a joint surgical system according to a first embodiment.

A first embodiment according to the present invention will now be described with reference to FIG. 1 to FIG. 4. As shown in FIG. 1, a joint surgical system 11 is used for a treatment between, e.g., a first bone 12 and a second bone 13 in a treatment target region, e.g., a joint of a shoulder, a knee, an elbow, or the like. The joint surgical system 11 includes a treatment tool 14, a power supply unit 15 as a power supply apparatus which operates the treatment tool 14, an endoscope apparatus 17 including an arthroscope 16, and a sensor 22 which can measure a temperature of a perfusate 21 which fills a joint cavity 18 at the time of surgery.

As shown in FIG. 1, the endoscope apparatus 17 includes the arthroscope 16, an image processing unit 23, and a display section 24 such as a display.

The arthroscope 16 includes an inserting section 25 and a holding section 26. In a treatment using the joint surgical system 11, a distal end portion of the inserting section 25 is inserted into the joint cavity 18. One end of a universal cord 27 is connected to the holding section 26. The other end of the universal cord 27 is connected to the image processing unit 23 such as an image processor. The image processing unit 23 is electrically connected to the display section 24 such as a monitor.

An imaging element is provided at a distal end portion of the inserting section 25. The imaging element images a subject through an observation window. The imaging element is electrically connected to the image processing unit 23 via an imaging cable extended through the inside of the inserting section 25, the inside of the holding section 26, and the inside of the universal cord 27. A captured subject image is subjected to image processing by the image processing unit 23. Further, the image-processed subject image is displayed in the display section 24. It is to be noted that a non-illustrated light source unit is connected to the arthroscope 16, and light emitted from the light source unit is applied to the subject.

The sensor 22 (a measurement section) is constituted of a generally available temperature sensor such as a thermocouple. This sensor 22 measures a temperature of the perfusate 21 in the joint cavity 18. For example, the sensor 22 is provided on a distal end portion of a sheath 28 of the later-described treatment tool 14 at a position where it comes into contact with the perfusate 21 in the joint cavity 18. The sensor 22 may be provided at a position of an end face 28B of a cylinder of the sheath 28 as shown in FIG. 1, may be provided on an inner peripheral surface of the cylinder of the sheath 28 near the end face 28B, or may be provided on an outer peripheral surface of the cylinder of the sheath 28 near the end face 28B. The sensor 22 may be provided at a position other than the treatment tool 14.

As shown in FIG. 1, the treatment tool 14 includes a case 31 which constitutes an outer shell, a vibration generating section 32 (a transducer) accommodated in the case 31, a rod-like probe 33 connected to the vibration generating section 32, a hollow (cylindrical) sheath 28 which covers the periphery of the probe 33 to protect the probe 33, a first insulating member which covers the inner peripheral surface of the sheath 28, a second insulating member which covers the outer peripheral surface of the sheath 28, and a plurality of buttons 45 and 46 provided on the case 31. It is to be noted that the description will be given on the assumption that an arrow D1 shown in FIG. 1 is a distal end direction of the probe 33 and an arrow D2 is a proximal end direction of the probe 33.

One end of a cable 35 is connected to the case 31. The other end of the cable 35 is connected to the power supply unit 15. A knob 34 is rotatably disposed at the periphery of a central axis C of the probe 33 to the case 31. This knob 34 is coupled with the probe 33 through a non-illustrated coupling mechanism. Thus, when the knob 34 is rotated to the case 31, the probe 33 can be integrally rotated around the central axis C. Consequently, an operator can rotate the probe 33 around the central axis C during surgery.

Figure 2:
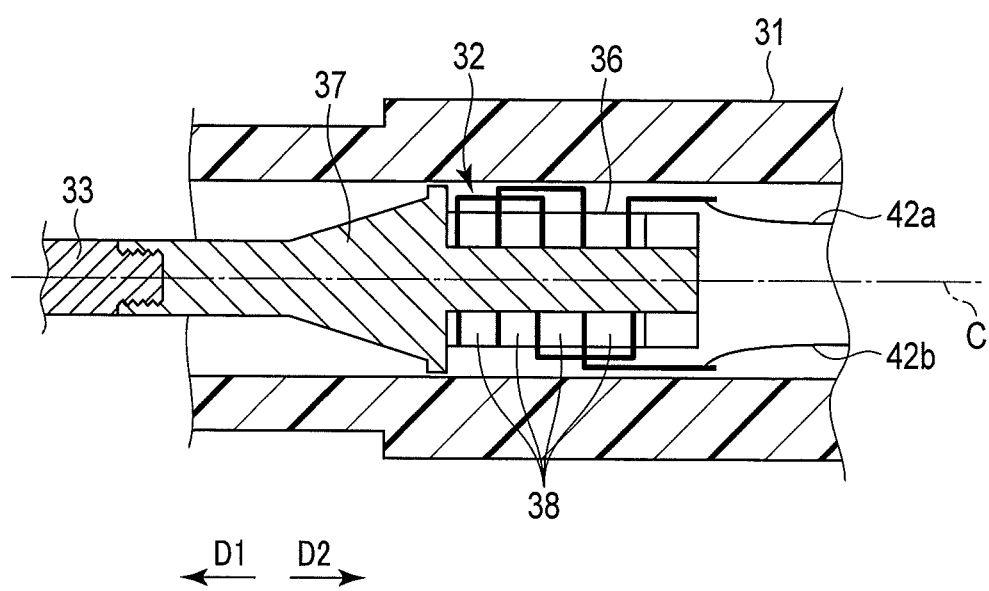
FIG. 2 is an enlarged cross-sectional view showing a vibration generating section and the vicinity thereof in a treatment tool of the joint surgical system depicted in FIG. 1.

As shown in FIG. 2, the vibration generating section 32 includes an ultrasonic vibrator 36 and a horn member 37. Piezoelectric elements 38 (which are, e.g., four in number in this embodiment) that change electric power (energy) into ultrasonic vibrations are provided on the ultrasonic vibrator 36. One end of each of first electrical wiring lines 42a and 42b is connected to the ultrasonic vibrator 36. The other ends of the first electrical wiring lines 42a and 42b are connected to an ultrasonic energy output section 41 in the power supply unit 15 through the inside of the cable 35. The ultrasonic energy output section 41 outputs electric power (ultrasonic energy) to drive the ultrasonic vibrator 36 through the first electrical wiring lines 42a and 42b. Consequently, the ultrasonic vibrator 36 generates the ultrasonic vibrations. It is to be noted that the first electrical wiring line 42a is connected to a positive pole of the ultrasonic energy output section 41, and the first electrical wiring line 42b is connected to a negative pole of the ultrasonic energy output section 41.

The ultrasonic vibrator 36 is disposed to the horn member 37. The horn member 37 is made of a metallic material. A substantially conical cross-section changing section whose cross-sectional area gradually decreases toward the distal end direction D1 of the probe 33 is provided to the horn member 37. The ultrasonic vibration generated by the ultrasonic vibrator 36 is transmitted to the horn member 37, and an amplitude of the ultrasonic vibration is increased by the cross-section changing section.

As shown in FIG. 1, the probe 33 is formed into a rod-like shape by using, e.g., a metallic material having biocompatibility (for example, a titanium alloy or the like). This probe 33 has a shaft section 43 (a main body section) extending in a rod-like shape. A treatment section 44 protruding in a rake-like shape (a hook-like shape) along a direction crossing an extending direction of the shaft section 43 is provided on a distal end side (a distal end portion) of this shaft section 43. A proximal end portion of the probe 33 (the shaft section 43) is coupled with the horn member 37. Thus, the probe 33 can transmit the ultrasonic vibration generated by the ultrasonic vibrator 36 and give a treatment to resect a bone by using the distal end portion (the treatment section 44) of the probe 33.

Furthermore, the probe 33 is electrically connected to one end of one of two second electrical wiring lines. The other end of the one second electrical wiring line is electrically connected to a high-frequency energy output section 47 in the power supply unit 15. Consequently, the probe 33 serves as one pole of a bipolar electrode which is configured to give a bipolar treatment. It is to be noted that, in this embodiment, the one second electrical wiring line is electrically connected to a negative pole of the high-frequency energy output section 47. Thus, the probe 33 configures a return electrode in the bipolar treatment.

The sheath 28 is made of a material having electrical conductivity which allows a high-frequency current to transmit therethrough. Moreover, the sheath 28 is electrically connected to one end of the other of the two second electrical wiring lines. The other end of the other second electrical wiring line is electrically connected to the high-frequency energy output section 47 of the power supply unit 15. Consequently, the sheath 28 serves as the other pole of the bipolar electrode to give the bipolar treatment. It is to be noted that, in this embodiment, the other second electrical wiring line is electrically connected to a positive pole of the high-frequency energy output section 47. Thus, the sheath 28 constitutes an active electrode in the bipolar treatment.

A first insulating member and a second insulating member are disposed to the sheath 28 or coat the same. The first insulating member and the second insulating member are coating films each having an insulating tube or an insulating material made of a synthetic resin material applied thereto. In this embodiment, the first insulating member covers the inner peripheral surface of the sheath 28, and the second insulating member 28 covers the outer peripheral surface. Consequently, the end face 28A of the sheath 28 provided at the distal end is solely exposed to the outside. Thus, the end face 28A of the sheath 28 as a partial region of the sheath 28 on the distal end side functions as the other pole of the bipolar electrode. Additionally, when the electrical power (the high-frequency energy) is output from the high-frequency energy output section 47, supplying the high-frequency energy from the end face 28A of the sheath 28 to the distal end portion of the probe 33 enables the bipolar treatment. In other words, the end face 28A of the sheath 28 functions as the active electrode, and the distal end portion of the probe 33 functions as the return electrode. In this manner, when the end face 28A of the sheath 28 is solely exposed to the outside and the remaining part of the same is covered with the first insulating member and the second insulating member as insulating members, the bipolar treatment can be performed between the end face 28A of the sheath 28 at the distal end and the distal end portion of the probe 33.

For example, two buttons 45 and 46 are provided on the case 31. Although the number of buttons is two, it may be three or more. The first button 45 corresponds to a coagulation/incision mode to incise or excise a bone or a biotissue while performing hemostasis (coagulation) to the biotissue. The second button 46 corresponds to a coagulation mode to give a treatment such as hemostatic when a bone or a biotissue has a hemorrhage.

As shown in FIG. 1, the power supply unit 15 has the ultrasonic energy output section 41 (the ultrasonic output section), the high-frequency energy output section 47 (the high-frequency output section), a control section 48 which controls these sections, and a sensing section (a second sensor) which can measure a room temperature. The control section 48 can control supply of the ultrasonic energy from the ultrasonic energy output section 41 and supply of the high-frequency energy from the high-frequency energy output section 47. That is, when an operator operates the first button 45, the control section 48 can output from the treatment section 14 (the probe 33, the sheath 28) either first energy suitable for incision or excision of a bone tissue (a biotissue) or second energy used as alternative energy of the first energy. Likewise, when the operator operates the second button 46, either third energy suitable for coagulation or hemostasis of the bone tissue (the biotissue) or fourth energy used as alternative energy of the third energy can be output from the treatment tool 14 (the probe 33, the sheath 28).

The first energy is energy including both the ultrasonic vibration (the ultrasonic energy) which vibrates with an amplitude generally used in an ultrasonic treatment (a normal amplitude) and the high-frequency current (the high-frequency energy). The second energy includes the ultrasonic vibration that vibrates with am amplitude which is, e.g., 20 to 40% higher than the normal amplitude, but it does not include the high-frequency current. The third energy includes the high-frequency current, but it does not include the ultrasonic vibration. The fourth energy includes the ultrasonic vibration that vibrates with an amplitude which is, e.g., 30 to 50% lower than the normal amplitude, but it does not include the high-frequency current.

When a temperature of the perfusate 21 measured by the sensor 22 is lower than a threshold value (a predetermined temperature) at the time of operating the first button 45, the control section 48 controls the ultrasonic energy output section 41 and the high-frequency energy output section 47 to output the first energy (the ultrasonic vibration, the high-frequency current) from the treatment section 14. On the other hand, when a temperature of the perfusate 21 measured by the sensor 22 is equal to or higher than the predetermined threshold value at the time of operating the first button 45, the control section 48 controls the ultrasonic energy output section 41 to output the second energy (the ultrasonic vibration) from the treatment tool 14. The threshold value is generally a temperature at which a biotissue is adversely affected by heat, and it is appropriately set to fall within a range of, e.g., 40° C. to 60° C. or more preferably a range of 45° C. to 50° C.

When a temperature of the perfusate 21 measured by the sensor 22 is lower than a predetermined threshold value at the time of operating the second button 46, the control section 48 controls the high-frequency energy output section 47 to output the third energy (the high-frequency current) from the treatment tool 14. On the other hand, when a temperature of the perfusate 21 measured by the sensor 22 is equal to or higher than the predetermined threshold value at the time of operating the second button 46, the control section 48 controls the ultrasonic energy output section 41 to output the fourth energy (the ultrasonic vibration) from the treatment tool. The threshold value which serves as a criterion for judgment to output either the third energy or the fourth energy when the second button 46 is operated is the same as the threshold value which serves as a criterion for judgment to output either the first energy or the second energy when the first button 45 is operated.

A function of the joint surgical system 11 (an arthroscopic surgery method using the joint surgical system 11) according to this embodiment will now be described with reference to FIG. 1 to FIG. 4.

As shown in FIG. 1, an operator inserts the inserting section 25 of the arthroscope 16 into the joint cavity 18. In a state where observation is performed with the use of the arthroscope 16, the sheath 28 and the probe 33 of the treatment tool 14 are inserted into the joint cavity 18. A tubular guide called cannula 51 which is arranged to pierce through a patient's skin in advance can be used for insertion of the arthroscope 16 and the treatment tool 14. Further, the ultrasonically-vibrated probe 33 can be used for removal of a part of a joint capsule A provided around the joint cavity 18. Thus, the same probe 33 as that used in a later-described treatment for the first bone 12 can be used, and the treatment tool 14 does not have to be replaced. Furthermore, prior to a treatment using the treatment tool 14, the joint cavity 18 is filled with a liquid having electrical conductivity (a liquid containing an electrolyte) such as an arthroscope perfusate consisting of a lactate Ringer's solution or a normal saline solution by a well-known method.

As shown in FIG. 1, the sheath 28 and the probe 33 are inserted between the first bone 12 and the second bone 13 which faces the first bone 12. The incision or excision treatment will now be described hereinafter with reference to a flowchart shown in FIG. 3. When the treatment section 44 of the probe 33 is arranged to abut on the first bone 12 as a treatment target and the operator operates the first button 45, the first energy (the ultrasonic vibration, the high-frequency current) can be given (a step S11). Consequently, the probe 33 and the treatment section 44 provided at the distal end thereof ultrasonically vibrate. At the same time, the high-frequency current output from the sheath 28 is supplied to pass through the perfusate and the first bone 12 and return to the treatment section 44 of the probe 33. The operator can give a treatment such as resecting an unfavorable part of the first bone 12 as the treatment target with the use of the probe 33 while finely adjusting positions and angles of the sheath 28 and the probe 33. This treatment includes various kinds of treatments, e.g., excision of a bone spur present on the first bone 12 and a cortical bone, a cartilage, and a cancellous bone present around the same, synovectomy, meniscectomy, removal of any other biotissue present around the first bone 12, and others. When the surgery is terminated without an increase in temperature of the perfusate 21 beyond the threshold value, the incision or excision treatment can be completed as it is (a step S12).

In the treatment of resecting the first bone 12, when the supply of the first energy is continued, the temperature of the perfusate 21 increases in proportion to a current flowing through the perfusate 21. Moreover, when the temperature of the perfusate 21 measured by the sensor 22 exceeds the threshold value, the control section 48 switches the energy to be supplied to the probe 33 from the first energy to the second energy (steps S13 and S14). Since the second energy is not supply of the high-frequency current but is the ultrasonic vibration alone, the temperature of the perfusate 21 does not keep increasing any longer. Thus, it is possible to avoid an increase in temperature of the perfusate 21 and prevent the patient's biotissue from being adversely affected by the high temperature. When the surgery is terminated in a state where the energy has been switched to the second energy, the incision or excision treatment can be completed as it is (a step S15).

Additionally, when the temperature of the perfusate 21 measured by the sensor 22 falls below a safe temperature which is 5° C. to 10° C. lower than the threshold value during the surgery in the state where the energy has been switched to the second energy, the control section 48 switches the energy to be supplied to the probe 22 from the second energy to the first energy (steps S16 and S11). When the incision or excision treatment is terminated in this state, the incision or excision treatment can be completed (a step S12).

On the other hand, when the operator has given a treatment to a tissue including a blood vessel (e.g., the first bone 12 or its surrounding tissue) and this tissue has had a hemorrhage, the operator can give a hemostatic treatment as required. The hemostatic treatment will now be described with reference to a flowchart shown in FIG. 4. In case of giving the hemostatic treatment, the operator arranges the end face 28A of the sheath 28 shown in FIG. 1 to abut on the tissue having the hemorrhage (e.g., the first bone 12 or its surrounding tissue). In this state, when the operator operates the second button 46, the third energy is supplied from the end face 28A of the sheath 28 (a step S11'). Since the third energy is constituted of the high-frequency current, the high-frequency current is supplied from the end face 28A of the sheath 28, and the tissue having the hemorrhage can be cauterized.

The high-frequency current supplied from the end face 28A of the sheath 28 is recovered by the probe 33 through the liquid having electrical conductivity filling the bone and the joint cavity 18. The high-frequency current recovered by the probe 33 is returned to the high-frequency energy output section 47. It is to be noted that, in this embodiment, since the end face 28A of the sheath 28 alone is not covered with the first insulating member and the second insulating member, the high-frequency current is concentrated on the end face 28A and the vicinity thereof, and the hemostatic treatment can be uneventfully given to the tissue having the hemorrhage even in an environment filled with the liquid having electrical conductivity. When the surgery is terminated in a state where the temperature of the perfusate 21 does not exceed the threshold value, the hemostatic treatment can be completed as it is (a step S12').

When the supply of the third energy is continued during the hemostatic treatment, the high-frequency current flows through the perfusate 21, and the temperature of the perfusate 21 increases. Further, when the temperature of the perfusate 21 measured by the sensor 22 reaches the threshold value or more, the control section 48 switches the energy to be supplied to the probe 33 from the third energy to the fourth energy (a step S13', a step S14'). Since the fourth energy is the ultrasonic vibration provided by reducing the amplitude to be smaller than the normal amplitude without flowing the high-frequency current, the temperature of the perfusate 21 does not keep increasing any longer. Thus, it is possible to avoid an increase in temperature of the perfusate 21 and prevent the patient's biotissue from being adversely affected by the high temperature. When the surgery is terminated in a state where the energy has been switched to the fourth energy, the hemostatic treatment can be completed as it is (a step S15').

Furthermore, during continuation of the hemostatic treatment in the state where the energy has been switched to the fourth energy, when the temperature of the perfusate 21 falls below the safe temperature which is, e.g., 5° C. to 10° C. lower than the threshold value, the control section 48 switches the energy to be supplied to the probe 33 from the fourth energy to the third energy (steps S16' and S11'). When the hemostatic treatment is terminated in this state, the hemostatic treatment can be finished (the step S12').

After the end of the hemostatic treatment, the operator can restart the incision/removal of an unfavorable part of the first bone 12 and its surrounding biotissue by using the treatment section 44 of the probe 33 on the basis of the flowchart of FIG. 3 as required. As described above, in this embodiment, the operator can perform the incision/excision treatment of a biotissue such as a bone and the hemostatic treatment in case of a hemorrhage by using the same treatment tool 14. Thus, there is no time loss from the hemorrhage to the actual hemostatic treatment, and the operator does not lose sight of a bleeding area. Moreover, since the control to switch the types of energy is performed when the temperature of perfusate 21 increases, a biotissue present around a treatment target region is not adversely affected by heat.

According to the first embodiment, the joint surgical system 11 includes the treatment section 14 which can give the high-frequency treatment using the high-frequency current and the ultrasonic treatment using the ultrasonic vibration to the treatment target region in the joint cavity 18 filled with the liquid having electrical conductivity, the high-frequency output section which outputs the high-frequency energy for the high-frequency treatment to the treatment section 44, the ultrasonic output section which outputs the ultrasonic energy for the ultrasonic treatment to the treatment tool 14, the measurement section which measures a temperature of the liquid, and the control section 48 which controls the high-frequency output section to stop output of the high-frequency energy and controls the ultrasonic output section to continue output of the ultrasonic energy when a measurement temperature measured by the measurement section is equal to or higher than a predetermined temperature.

Usually, the perfusate such as a lactate Ringer's solution or a normal saline solution used in an arthroscopic surgery contains an electrolyte, and hence it has electrical conductivity. Thus, when a treatment to flow a high-frequency current through a biotissue in the arthroscopic surgery (the high-frequency treatment) is continuously performed for a long time, there occurs a problem that a temperature of the perfusate increases. Thus, when a temperature of the perfusate 21 reaches a certain temperature or more, there is a possibility that a patient's biotissue is adversely affected by heat. On the other hand, in the ultrasonic treatment using the ultrasonic vibration, since a temperature of the perfusate 21 does not increase, the operator can continue a safe treatment by using the ultrasonic vibration.

According to the above-described configuration, when a temperature of the perfusate 21 measured by the measurement section increases a predetermined temperature or more, since the control section 48 performs the control to stop output of the high-frequency energy and to continue output of the ultrasonic energy, it is possible to avoid a further increase in temperature of the perfusate 21 and prevent a surrounding biotissue from being adversely affected by high heat. Consequently, the surgery can be safely conducted. Additionally, the surgery can be continued even in a state where the temperature of the perfusate 21 has increased to some extent, and it is possible to prevent the surgery from being stopped or performance in a treatment of the operator from being lowered. Thus, it is possible to avoid prolonging an anesthesia time due to an extension of a surgery time or reducing concentration power of the operator.

In this case, when the measurement temperature is equal to or higher than the predetermined temperature, the control section 48 controls the ultrasonic output section to increase the ultrasonic energy to be higher than that in a state where the measurement temperature is the predetermined temperature or less. According to this configuration, mainly in a treatment to incise or excise a treatment target region, when a temperature of the perfusate 21 is equal to or higher than the predetermined temperature and output of the high-frequency energy is stopped, an energy amount suitable for the incision or the excision can be assured by increasing output of the ultrasonic energy. Consequently, a treatment (the incision, the excision) comparable to a counterpart before the temperature of the perfusate 21 exceeds the predetermined temperature can be performed. As a result, the operator's convenience can be improved, and a surgery time can be shortened.

In this case, when the measurement temperature is equal to or higher than the predetermined temperature, the control section 48 controls the ultrasonic output section to decrease the ultrasonic energy to be lower than that in the state where the measurement temperature is the predetermined temperature or less. According to this configuration, mainly in a treatment to coagulate a treatment target region, when the temperature of the perfusate 21 is equal to or higher than the predetermined temperature and output of the high-frequency energy is stopped, an energy amount suitable for the coagulation can be provided by decreasing output of the ultrasonic energy. Consequently, a treatment (the coagulation) which is comparable to a counterpart before the temperature of the perfusate exceeds the predetermined temperature can be carried out.

The measurement section is provided at a position on the treatment tool 14 where it comes into contact with the liquid. According to this configuration, a temperature of the liquid can be accurately measured by the measurement section.

Modification of First Embodiment

A modification of the joint surgical system 11 according to the first embodiment will now be described with reference to FIG. 5. Although a first modification is different from the first embodiment in that the sensor 22 (the measurement section) is not provided, other structures are equal to those in the first embodiment. Thus, parts different from the first embodiment will be mainly described, and an illustration or a description on parts equal to the first embodiment will be omitted.

The power supply unit 15 has the ultrasonic energy output section 41 (the ultrasonic output section), the high-frequency energy output section 47, the control section 48 which controls these sections, and sensing section (a second sensor) which can measure a room temperature. The control section 48 can control supply of the ultrasonic energy from the ultrasonic energy output section 41 and supply of the high-frequency energy from the high-frequency energy output section 47.

That is, when the operator operates the first button 45, the control section 48 can output from the treatment tool 14 (the probe 33, the sheath 28) either the first energy suitable for incision or excision of a bone tissue (a biotissue) or second energy used as alternative energy of the first energy. Likewise, when the operator operates the second button 46, it can output from the treatment tool (the probe 33, the sheath 28) either the third energy suitable for coagulation or hemostasis of the bone tissue (the biotissue) or the fourth energy used as alternative energy of the third energy. Compositions of the first energy to the fourth energy are the same as those in the first embodiment.

The control section 48 has an algorithm (software) that enables estimating a temperature of the perfusate 21, which has increased beyond a room temperature, on the basis of a supply time for which a high-frequency current is supplied to the perfusate 21. According to this algorithm, a quantity of heat to be generated can be calculated from the supply time of the high-frequency energy, and a current temperature of the perfusate 21 can be calculated as an estimated temperature from specific heat of the perfusate 21, a liquid volume of the perfusate 21, a room temperature, and others.

When the estimated temperature of the perfusate 21 is lower than a threshold value (a predetermined temperature) at the time of operating the first button 45, the control section 48 controls the ultrasonic energy output section 41 and the high-frequency energy output section 47 to output the first energy (the ultrasonic vibration, the high-frequency current) from the treatment tool 14. On the other hand, when the estimated temperature of the perfusate 21 is equal to or higher than the predetermined threshold value at the time of operating the first button 45, the control section 48 controls the ultrasonic energy output section 41 to output the second energy (the ultrasonic vibration) from the treatment tool 14. The threshold value is the same as that in the first embodiment.

When the estimated temperature of the perfusate 21 is lower than the threshold value at the time of operating the second button 46, the control section 48 controls the high-frequency energy output section 47 to output the third energy (the high-frequency current) from the treatment tool 14. On the other hand, when the estimated temperature of the perfusate 21 is equal to or higher than the predetermined threshold value at the time of operating the second button 46, the control section 48 controls the ultrasonic energy output section 41 to output the fourth energy (the ultrasonic vibration) from the treatment tool 14. The threshold value which serves as a criterion for judgment to output either the third energy or the fourth energy when the second button 46 is operated is the same as the above-described threshold value. The incision/excision treatment and the hemostatic treatment according to this modification are different from those of the first embodiment in that whether the temperature of the perfusate 21 is equal to or higher than the threshold value and whether the temperature of the perfusate 21 falls below the safe temperature are determined on the basis of an estimated temperature calculated by the control section 48 rather than a temperature actually measured by the sensor 22, but other processes are carried out in the same procedure as that of the first embodiment.

According to this modification, the joint surgical system 11 includes the treatment tool 14 which can give the high-frequency treatment using the high-frequency current and the ultrasonic treatment using the ultrasonic vibration to the treatment target region in the joint cavity 18 filled with the liquid having electrical conductivity, the high-frequency output section which outputs the high-frequency energy for the high-frequency treatment to the treatment tool 44, the ultrasonic output section outputs the ultrasonic energy for the ultrasonic treatment to the treatment tool 14, and the control section 48 controls the high-frequency output section to stop output of the high-frequency current and controls the ultrasonic output section to continue output of the ultrasonic vibration when an estimated temperature obtained by estimation is equal to or higher than a predetermined temperature.

According to this configuration, when an estimated temperature of the perfusate 21 measured by the measurement section is equal to or higher than the predetermined temperature, the control section 48 can conduct the control to stop output of the high-frequency energy and to continue output of the ultrasonic energy. Consequently, it is possible to prevent a surrounding biotissue from being adversely affected by high heat caused by a continuous increase in temperature of the perfusate 21. Further, since the measurement section (the sensor 22) can be omitted, manufacturing costs can be reduced as compared with the joint surgical system 11 according to the first embodiment.

In this case, when the estimated temperature is equal to or higher than the predetermined temperature, the control section 48 controls the ultrasonic output section to increase the ultrasonic energy to be higher than that in a state where the estimated temperature is equal to or lower than the predetermined temperature. According to this configuration, mainly in a treatment to incise or excise a treatment target region, when an estimated temperature of the perfusate 21 is equal to or higher than the predetermined temperature and output of the high-frequency energy is stopped, an energy amount suitable for the incision or the excision can be assured by increasing output of the ultrasonic energy. Consequently, a treatment (the incision, the excision) comparable to a counterpart before the estimated temperature of the perfusate 21 exceeds the predetermined temperature can be performed. As a result, the operator's convenience can be improved, and a surgery time can be shortened.

In this case, when the estimated temperature is equal to or higher than the predetermined temperature, the control section 48 controls the ultrasonic output section to decrease the ultrasonic energy to be lower than that in the state where the estimated temperature is the predetermined temperature or less. According to this configuration, mainly in a treatment to coagulate a treatment target region, when the estimated temperature of the perfusate 21 is equal to or higher than the predetermined temperature and output of the high-frequency energy is stopped, an energy amount suitable for the coagulation can be provided by decreasing output of the ultrasonic energy. Consequently, a treatment (the coagulation) which is comparable to a counterpart before the estimated temperature of the perfusate 21 exceeds the predetermined temperature can be carried out.

Second Embodiment

Figure 8:
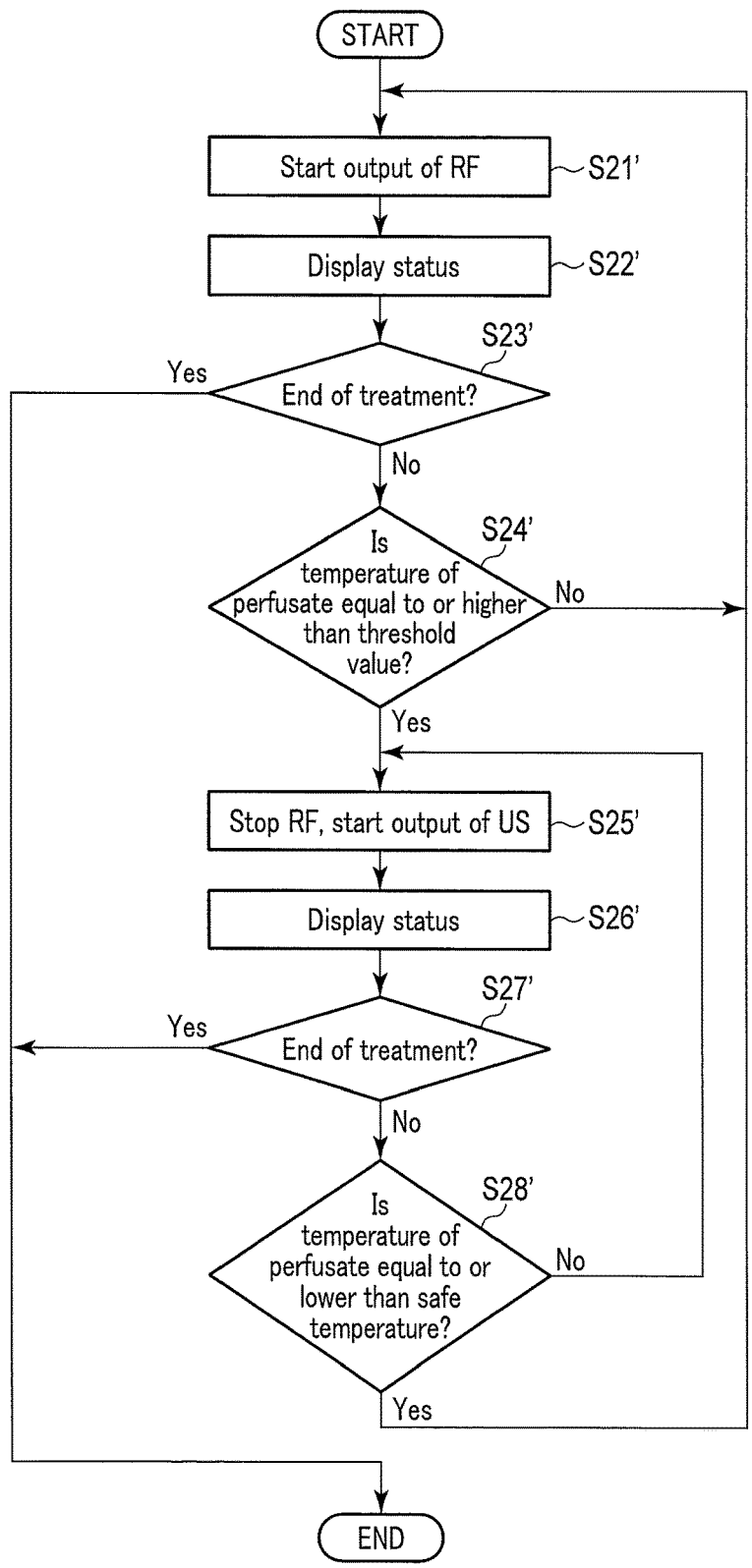
FIG. 8 is a flowchart showing a procedure of a hemostatic treatment using the joint surgical system depicted in FIG. 6.

A joint surgical system according to a second embodiment will now be described with reference to FIG. 6 to FIG. 8. A joint surgical system 11 according to the second embodiment is different from that according to the first embodiment in that a status such as a temperature of a perfusate 21 sensed by a sensor 22 or the like is displayed in a display section 24, but other structures are the same as those of the first embodiment. Thus, parts different from the first embodiment will be mainly described, and an illustration or a description on the same parts as the first embodiment will be omitted.

Figure 6:
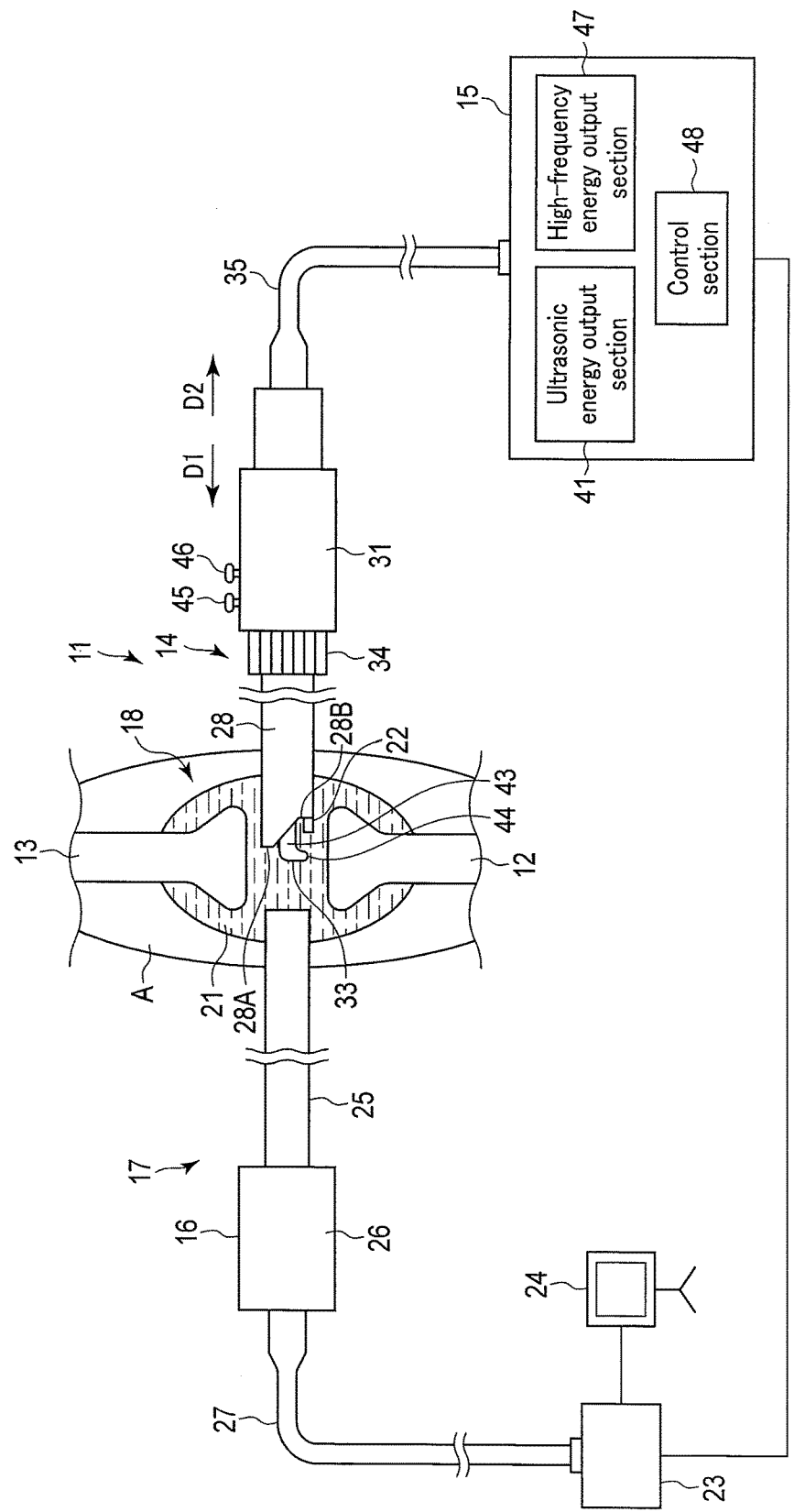
FIG. 6 is a schematic view showing a joint surgical system according to a second embodiment.

As shown in FIG. 6, a power supply unit 15 has an ultrasonic energy output section 41 (an ultrasonic output section), a high-frequency energy output section 47 (a high-frequency output section), a control section 48 which controls these sections, and a sensing section (a second sensor) which can measure a room temperature. The control section 48 can control supply of the ultrasonic energy from the ultrasonic energy output section 41 and supply of the high-frequency energy from the high-frequency energy output section 47.

That is, when an operator operates a first button 45, the control section 48 can output from a treatment tool 14 (a probe 33, a sheath 28) either first energy suitable for incision or excision of a bone tissue (a biotissue) or second energy used as alternative energy of the first energy. Likewise, when the operator operates a second button 46, it can output from the treatment tool 14 (the probe 33, the sheath 28) either third energy suitable for coagulation or hemostasis of the bone tissue (the biotissue) or fourth energy used as alternative energy of the third energy. Compositions of the first energy to the fourth energy are the same as those in the first embodiment.

The control section 48 can display an output state of a high-frequency current (high-frequency energy) and an oscillation state of ultrasonic vibration (ultrasonic energy) in the display section 24. More specifically, the control section 48 can display an amplitude, a frequency, and others of the ultrasonic vibration in the display section. Additionally, the control section 48 can display various kinds of statuses such as a current temperature of a perfusate 21, the number of times of supplying the high-frequency current up to now, a total supply time of the high-frequency current, a voltage (intensity) of the high-frequency current, and others in the display section 24.

When a temperature of the perfusate 21 is lower than a threshold value (a predetermined temperature) at the time of operating the first button 45, the control section 48 controls the ultrasonic energy output section 41 and the high-frequency energy output section 47 to output the first energy (the ultrasonic vibration, the high-frequency current) from the treatment tool 14. On the other hand, when a temperature of the perfusate 21 is equal to or higher than the predetermined threshold value at the time of operating the first button 45, the control section 48 controls the ultrasonic energy output section 41 to output the second energy (the ultrasonic vibration) from the treatment tool 14. The threshold value is generally a temperature at which a biotissue is adversely affected by heat, and it is appropriately set to fall within a range of, e.g., 40° C. to 60° C. or more preferably a range of 45° C. to 50° C.

When a temperature of the perfusate 21 is lower than a predetermined threshold value at the time of operating the second button 46, the control section 48 controls the high-frequency energy output section 47 to output the third energy (the high-frequency current) from the treatment tool 14. On the other hand, when a temperature of the perfusate 21 is equal to or higher than the predetermined threshold value at the time of operating the second button 46, the control section 48 controls the ultrasonic energy output section 41 to output the fourth energy (the ultrasonic vibration) from the treatment tool 14. The threshold value which serves as a criterion for judgment to output either the third energy or the fourth energy when the second button 46 is operated is the same as the threshold value which serves as a criterion for judgment to output either the first energy or the second energy when the first button 45 is operated.

A function of the joint surgical system 11 (an arthroscopic surgery method using the joint surgical system 11) according to this embodiment will now be described with reference to FIG. 6 to FIG. 8.

As shown in FIG. 6, an operator inserts an inserting section 25 of an arthroscope 16 into a joint cavity 18. In a state where observation is performed with the use of the arthroscope 16, the sheath 28 and the probe 33 of the treatment tool 14 are inserted into the joint cavity 18. Furthermore, prior to a treatment using the treatment tool 14, the joint cavity 18 is filled with a liquid having electrical conductivity (a liquid containing an electrolyte) such as an arthroscope perfusate consisting of a lactate Ringer's solution or a normal saline solution by a well-known method.

As shown in FIG. 6, the sheath 28 and the probe 33 are inserted between a first bone 12 and a second bone 13 which faces the first bone 12. The incision or excision treatment will now be described with reference to a flowchart shown in FIG. 7 hereinafter. When the treatment section 44 of the probe 33 is arranged to abut on the first bone 12 as a treatment target and the operator operates the first button 45, the first energy (the ultrasonic vibration, the high-frequency current) can be given to the probe 33 (a step S21). Consequently, the probe 33 and the treatment section 44 provided at the distal end thereof ultrasonically vibrate. At the same time, the high-frequency current output from the sheath 28 is supplied to pass through the perfusate 21 and the first bone 12 and return to the treatment section 44 of the probe 33.

The operator can give a treatment such as resecting an unfavorable part of the first bone 12 as the treatment target with the use of the probe 33 while finely adjusting positions and angles of the sheath 28 and the probe 33. This treatment includes various kinds of treatments, e.g., removal of a bone spur present on the first bone 12, any other biotissue present around the first bone 12, and others. In such an incision/excision treatment, the control section 48 can display various kinds of statuses, e.g., a current temperature of the perfusate 21, an output state of the ultrasonic energy of the treatment tool 14, an output state of the high-frequency energy of the treatment tool 14, and others in the display section 24 (a step S22). When the surgery is terminated without an increase in temperature of the perfusate 21 beyond the threshold value, the incision or excision treatment can be completed as it is (a step S23).

In the treatment of resecting the first bone 12, when the supply of the first energy is continued, the temperature of the perfusate 21 increases in proportion to a current flowing through the perfusate 21. Moreover, when the temperature of the perfusate 21 exceeds the threshold value, the control section 48 switches the energy to be supplied to the probe 33 from the first energy to the second energy (steps S24 and S25). Since the second energy is not supply of the high-frequency current but is the ultrasonic vibration alone, the temperature of the perfusate 21 does not keep increasing any longer. Thus, it is possible to avoid an increase in temperature of the perfusate 21 and prevent a patient's biotissue from being adversely affected by the high temperature.

In a state after the control section 48 has switched the first energy to the second energy, the control section 48 can display various kinds of statuses, e.g., a current temperature of the perfusate 21, an output state of the ultrasonic energy of the treatment tool 14, an output state of the high-frequency energy of the treatment tool 14, and others in the display section 24 (a step S26). When the surgery is terminated in the state where the energy has been switched to the second energy, the incision or excision treatment can be completed as it is (a step S27).

Additionally, when the temperature of the perfusate 21 falls below a safe temperature which is, e.g., 5° C. to 10° C. lower than the threshold value during the surgery in the state where the energy has been switched to the second energy, the control section 48 switches the energy to be supplied to the probe 33 from the second energy to the first energy (steps S28 and S21). In the state after the control section 48 has switched the second energy to the first energy, the control section 48 can display various kinds of statuses, e.g., a current temperature of the perfusate 21, an output state of the ultrasonic energy of the treatment tool 14, an output state of the high-frequency energy of the treatment tool 14, and others in the display section 24 (the step S22). When the incision or excision treatment is terminated in this state, the incision or excision treatment can be completed (a step S23).

On the other hand, when the operator has given a treatment to a tissue including a blood vessel (e.g., the first bone 12 or its surrounding tissue) and this tissue has had a hemorrhage, the operator can give a hemostatic treatment as required. The hemostatic treatment will now be described hereinafter with reference to a flowchart shown in FIG. 8. In case of giving the hemostatic treatment, the operator arranges an end face 28A of the sheath 28 shown in FIG. 6 to abut on the tissue having the hemorrhage (e.g., the first bone 12 or its surrounding tissue). In this state, when the operator operates the second button 46, the third energy is supplied from the end face 28A of the sheath 28 (a step S21'). Since the third energy is constituted of the high-frequency current, the high-frequency current is supplied from the end face 28A of the sheath 28, and the tissue having the hemorrhage can be cauterized.

The high-frequency current supplied from the end face 28A of the sheath 28 is recovered by the probe 33 through the liquid having electrical conductivity filling the bone and the joint cavity 18. The high-frequency current recovered by the probe 33 is returned to the high-frequency energy output section 47. In such a hemostatic treatment, the control section 48 can display various kinds of statuses, e.g., a current temperature of the perfusate, an output state of the ultrasonic energy of the treatment tool 14, an output state of the high-frequency energy of the treatment tool 14, and others in the display section 24 (a step S22'). When the surgery is terminated in a state where the temperature of the perfusate 21 does not exceed the threshold value, the hemostatic treatment can be completed as it is (a step S23').

When the supply of the third energy is continued during the hemostatic treatment, the high-frequency current flows through the perfusate 21, and the temperature of the perfusate 21 increases. Further, when the temperature of the perfusate 21 reaches the threshold value or more, the control section 48 switches the energy to be supplied to the probe 33 from the third energy to the fourth energy (a step S24', a step S25'). Since the fourth energy is the ultrasonic vibration provided by reducing the amplitude to be smaller than the normal amplitude without flowing the high-frequency current, the temperature of the perfusate 21 does not keep increasing any longer. In a state after the control section 48 has switched the third energy to the fourth energy, the control section 48 can display various kinds of statuses, e.g., a current temperature of the perfusate 21, an output state of the ultrasonic energy of the treatment tool 14, an output state of the high-frequency energy of the treatment tool 14 (a state where output of the high-frequency energy is stopped), and others in the display section 24 (a step S26'). When the surgery is terminated in a state where the energy has been switched to the fourth energy, the hemostatic treatment can be completed as it is (a step S27').

Furthermore, during continuation of the hemostatic treatment in the state where the energy has been switched to the fourth energy, when the temperature of the perfusate 21 falls below the safe temperature which is, e.g., 5° C. to 10° C. lower than the threshold value, the control section 48 switches the energy to be supplied to the probe 33 from the fourth energy to the third energy (steps S28' and S21'). In a state after the control section 48 has switched the fourth energy to the third energy, the control section 48 can display various kinds of statuses, e.g., a current temperature of the perfusate 21, an output state of the ultrasonic energy of the treatment tool 14, an output state of the high-frequency energy of the treatment tool 14, and others in the display section 24 (the step S22'). When the hemostatic treatment is terminated in this state, the hemostatic treatment can be finished (the step S23').

After the end of the hemostatic treatment, the operator can restart the incision/removal of an unfavorable part of the first bone and its surrounding biotissue by using the treatment section 44 of the probe on the basis of the flowchart of FIG. 3 as required. As described above, in this embodiment, the operator can perform the incision/excision treatment of a biotissue, e.g., a bone or the like and the hemostatic treatment in case of a hemorrhage by using the same treatment tool 14. Moreover, since the control to switch the types of energy is performed when the temperature of perfusate 21 increases, a biotissue present around a treatment target region is not adversely affected by heat.

According to this embodiment, the joint surgical system 11 includes the endoscope apparatus 17 which allows visual confirmation of the treatment target region and the display section 24 which displays video images taken by the endoscope apparatus 17, and the control section 48 displays the measurement temperature in the display section 24. According to this configuration, the operator can confirm the measurement temperature measured by the measurement section in the display section 24. Thus, since the operator can grasp a temperature of the perfusate 21 and then conduct surgery, the surgery can be safely carried out, and the operator's convenience can be improved.

It is to be noted that, in this embodiment, when a temperature of the perfusate 21 is equal to or higher than the threshold value, the control section 48 automatically switches between the first energy and the second energy and switches between the third energy and the fourth energy, but the operator may manually perform such switching operations on the basis of a measurement temperature displayed in the display section 24 or display of a warning showing that the perfusate 21 has a high temperature.

Modification of Second Embodiment

Figure 9:
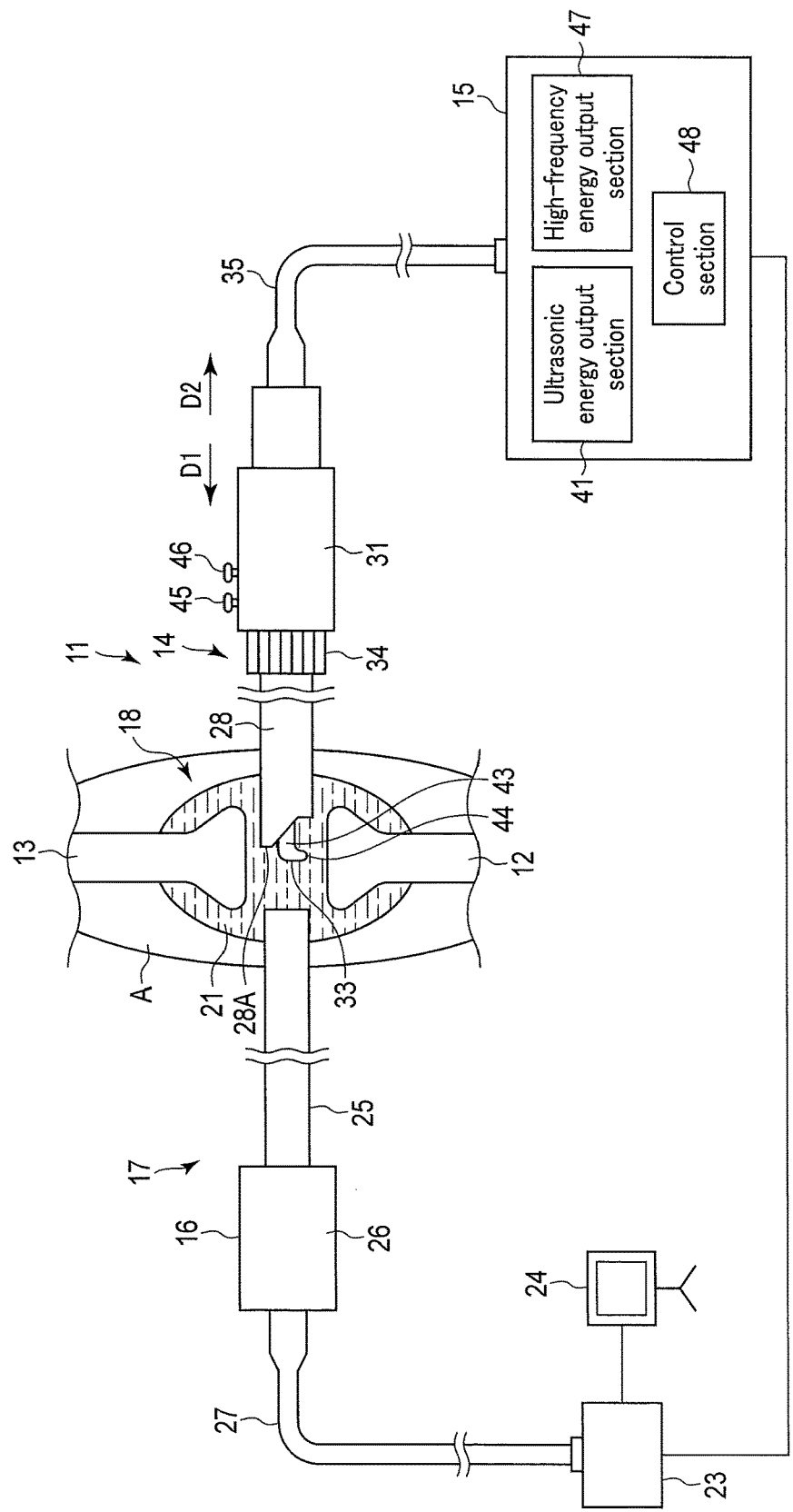
FIG. 9 is a schematic view showing a modification of a joint surgical system according to a modification of the second embodiment.

A modification of the joint surgical system 11 according to the second embodiment will now be described with reference to FIG. 9. Although the modification is different from the second embodiment in that the sensor 22 (the measurement section) is not provided, but other structures are the same as those in the second embodiment. Thus, parts different from the second embodiment will be mainly described, and an illustration or a description on parts equal to the second embodiment will be omitted.

The power supply unit 15 has the ultrasonic energy output section 41 (the ultrasonic output section), the high-frequency energy output section 47 (the high-frequency output section), the control section 48 which controls these sections, and the sensing section (a second sensor) which can measure a room temperature. The control section 48 can control supply of the ultrasonic energy from the ultrasonic energy output section 41 and supply of the high-frequency energy from the high-frequency energy output section 47.

That is, when the operator operates the first button 45, the control section 48 can output from the treatment tool 14 (the probe 33, the sheath 28) either the first energy suitable for incision or excision of a bone tissue (a biotissue) or the second energy used as alternative energy of the first energy. Likewise, when the operator operates the second button 46, it can output from the treatment section 14 (the probe 33, the sheath 28) either the third energy suitable for coagulation or hemostasis of the bone tissue (the biotissue) or the fourth energy used as alternative energy of the third energy. Compositions of the first energy to the fourth energy are the same as those in the second embodiment.

The control section 48 has an algorithm (software) that enables estimating a temperature of the perfusate 21, which has increased beyond a room temperature, on the basis of a supply time for which a high-frequency current is supplied to the perfusate 21. According to this algorithm, a quantity of heat to be generated can be calculated from the supply time of the high-frequency energy, and a current temperature of the perfusate 21 can be calculated as an estimated temperature from specific heat of the perfusate 21, a liquid volume of the perfusate 21, a room temperature, and others.

The control section 48 can display an output state of the high-frequency current (the high-frequency energy) and an oscillation state of the ultrasonic vibration (the ultrasonic energy) in the display section 24. More specifically, the control section 48 can display an amplitude, a frequency, and others of the ultrasonic vibration in the display section 24. Additionally, the control section 48 can display a current estimated temperature of a perfusate 21, the number of times of supplying the high-frequency current, a total supply time of the high-frequency current, a voltage (intensity) of the high-frequency current, and others in the display section 24.

When the estimated temperature of the perfusate 21 is lower than a threshold value (a predetermined temperature) at the time of operating the first button 45, the control section 48 controls the ultrasonic energy output section 41 and the high-frequency energy output section 47 to output the first energy (the ultrasonic vibration, the high-frequency current) from the treatment tool 14. On the other hand, when the estimated temperature of the perfusate 21 is equal to or higher than the predetermined threshold value at the time of operating the first button 45, the control section 48 controls the ultrasonic energy output section 41 to output the second energy (the ultrasonic vibration) from the treatment tool 14. The threshold value is the same as that in the second embodiment.

When the estimated temperature of the perfusate 21 is lower than the threshold value at the time of operating the second button 46, the control section 48 controls the high-frequency energy output section 47 to output the third energy (the high-frequency current) from the treatment tool 14. On the other hand, when the estimated temperature of the perfusate 21 is equal to or higher than the predetermined threshold value at the time of operating the second button 46, the control section 48 controls the ultrasonic energy output section 41 to output the fourth energy (the ultrasonic vibration) from the treatment tool 14. The threshold value which serves as a criterion for judgment to output either the third energy or the fourth energy when the second button 46 is operated is the same as the above-described threshold value. The incision/excision treatment and the hemostatic treatment according to this modification are different from those of the second embodiment in that whether the temperature of the perfusate 21 is equal to or higher than the threshold value is determined on the basis of an estimated temperature calculated by the control section 48 rather than a temperature actually measured by the sensor 22, but other processes are carried out in the same procedure as that of the second embodiment. The control section 48 can display the calculated estimated temperature in the display section 24 together with other statuses, e.g., an output state of the energy of the treatment section 14.

According to this embodiment, the joint surgical system 11 includes the endoscope apparatus 17 which allows visual confirmation of the treatment target region and the display section 24 which displays video images taken by the endoscope apparatus 17, and the control section 48 displays the estimated temperature in the display section 24. According to this configuration, the operator can confirm the measurement temperature measured by the measurement section in the display section 24. Thus, since the operator can grasp a temperature of the perfusate 21 and then conduct surgery, the surgery can be safely carried out, and the operator's convenience can be improved.

It is to be noted that, in this embodiment, when an estimated temperature of the perfusate 21 is equal to or higher than the threshold value, the control section 48 automatically switches between the first energy and the second energy and switches between the third energy and the fourth energy, but the operator may manually perform such switching operations on the basis of the estimated temperature displayed in the display section 24 or display of a warning showing that the perfusate 21 has a high temperature.

Third Embodiment

A joint surgical system according to a third embodiment will now be described with reference to FIG. 10 to FIG. 12. A joint surgical system 11 according to the third embodiment is different from that according to the second embodiment in that a status such as a temperature of a perfusate 21 sensed by a sensor 22 or the like and estimation information such as a temperature estimated from a measurement temperature are displayed in a display section 24, but other structures are the same as those of the second embodiment. Thus, parts different from the second embodiment will be mainly described, and an illustration or a description on the same parts as the second embodiment will be omitted. The joint surgical system 11 according to the third embodiment has the same appearance as that of the joint surgical system 11 according to the second embodiment depicted in FIG. 6.

A control section 48 can display an output state of a high-frequency current (high-frequency energy) and an oscillation state of ultrasonic vibration (ultrasonic energy) in the display section 24. More specifically, the control section 48 can display an amplitude, a frequency, and others of the ultrasonic vibration in the display section 24. Additionally, the control section 48 can display the number of times of supplying the high-frequency current, a total supply time of the high-frequency current, a voltage (intensity) of the high-frequency current, and others in the display section 24.

Further, the control section 48 can calculate an estimated time required for a perfusate 21 to eventually reach a threshold value from a room temperature, a total supply time of the high-frequency current up to now, specific heat of the perfusate 21, a liquid volume of the perfusate 21, a current temperature of the perfusate 21, and others. In a state before a treatment is started, a temperature of the perfusate 21 is a room temperature (r.t.). The control section 48 measures the room temperature by using a sensing section, and calculates an inclination of a straight line from the total supply time of the high-frequency current, the specific heat of the perfusate 21, the liquid volume of the perfusate 21, the current temperature of the perfusate 21, and others. The control section 48 can create a graph of the straight line as shown in FIG. 10, and can calculate the estimated time required for the perfusate 21 to reach a threshold temperature by a method of obtaining an intersection of the graph of the straight line and a straight line of the threshold temperature. The control section 48 calculates the estimated time and a remaining time before the estimated time, and then displays the remaining time like "the high-frequency energy can be used for . . . minutes (or . . . seconds)". When the remaining time is elapsed, the control section 48 can display information indicative of switching to the ultrasonic vibration (the ultrasonic energy) in the display section 24. The estimated time and the remaining time are examples of estimation information displayed in the display section 24.

When a temperature of the perfusate 21 is lower than a threshold value (a predetermined temperature) at the time of operating a first button 45, the control section 48 controls an ultrasonic energy output section 41 and a high-frequency energy output section 47 to output first energy (the ultrasonic vibration, the high-frequency current) from a treatment tool 14. On the other hand, when the temperature of the perfusate 21 is equal to or higher than the predetermined threshold value at the time of operating the first button 45, the control section 48 controls the ultrasonic energy output section 41 to output second energy (the ultrasonic vibration) from the treatment tool 14. The threshold value is the same as that in the second embodiment.

When the temperature of the perfusate 21 is lower than the threshold value at the time of operating a second button 46, the control section 48 controls the high-frequency energy output section 47 to output third energy (the high-frequency current) from the treatment tool 14. On the other hand, when the temperature of the perfusate 21 is equal to or higher than the predetermined threshold value at the time of operating the second button 46, the control section 48 controls the ultrasonic energy output section 41 to output fourth energy (the ultrasonic vibration) from the treatment tool 14. The threshold value which serves as a criterion for judgment to output either the third energy or the fourth energy when the second button 46 is operated is the same as the above-described threshold value.

A function of the joint surgical system 11 (an arthroscopic surgery method using the joint surgical system 11) according to this embodiment will now be described with reference to FIG. 11 and FIG. 12.

As shown in FIG. 6, an operator inserts an inserting section 25 of an arthroscope 16 into a joint cavity 18. In a state where observation is performed with the use of the arthroscope 16, a sheath 28 and a probe 33 of the treatment tool 14 are inserted into the joint cavity 18. Furthermore, prior to a treatment using the treatment tool 14, the joint cavity 18 is filled with a liquid having electrical conductivity (a liquid containing an electrolyte) such as an arthroscope perfusate consisting of a lactate Ringer's solution or a normal saline solution by a well-known method.

As shown in FIG. 6, the sheath 28 and the probe 33 are inserted between a first bone 12 and a second bone 13 which faces the first bone 12. The incision or excision treatment will now be described hereinafter with reference to a flowchart shown in FIG. 11. When the treatment section 44 of the probe 33 is arranged to abut on the first bone 12 as a treatment target and the operator operates the first button 45, the first energy (the ultrasonic vibration, the high-frequency current) can be given to the probe 33 (a step S31). Consequently, the probe 33 and the treatment section 44 provided at the distal end thereof ultrasonically vibrate. At the same time, the high-frequency current output from the sheath 28 is supplied to pass through the perfusate 21 and the first bone 12 and return to the treatment section 44 of the probe 33.

The operator can give a treatment such as resecting an unfavorable part of the first bone 12 as the treatment target with the use of the probe 33 while finely adjusting positions and angles of the sheath 28 and the probe 33. In such an incision/excision treatment, the control section 48 can display various kinds of statuses, e.g., output states of the ultrasonic energy and the high-frequency energy of the treatment tool 14, an estimated time required for the perfusate 21 to reach a threshold time, a remaining time before the estimated time, and others in the display section 24 (a step S32). Likewise, the control section 48 displays the estimated time required for the perfusate 21 to reach the threshold value and the remaining time before the estimated time (the step S32). When the surgery is terminated without an increase in temperature of the perfusate 21 beyond the threshold value, the incision or excision treatment can be completed as it is (a step S33).

In a treatment of resecting the first bone 12, when the supply of the first energy is continued, a temperature of the perfusate 21 increases in proportion to a current flowing through the perfusate 21. Moreover, when the temperature of the perfusate 21 exceeds the threshold value, the control section 48 switches the energy to be supplied to the probe 33 from the first energy to the second energy (steps S34 and S35).

In a state after the control section 48 has switched the first energy to the second energy, the control section 48 can display various kinds of statuses, e.g., an output state of the ultrasonic energy of the treatment tool 14, an output state of the high-frequency energy of the treatment tool 14, and others in the display section 24 (a step S36). When the surgery is terminated in the state where the energy has been switched to the second energy, the incision or excision treatment can be completed as it is (a step S37).

Additionally, when the temperature of the perfusate 21 falls below a safe temperature which is, e.g., 5° C. to 10° C. lower than the threshold value during the surgery in the state where the energy has been switched to the second energy, the control section 48 switches the energy to be supplied to the probe 33 from the second energy to the first energy (steps S38 and S31). In the state after the control section 48 has switched the second energy to the first energy, the control section 48 can display various kinds of statuses, e.g., an output state of the ultrasonic energy of the treatment tool 14, an output state of the high-frequency energy of the treatment tool 14, and others, the estimated time required for the perfusate 21 to reach the threshold value, and the remaining time before the estimated time in the display section 24 (the step S32). When the incision or excision treatment is terminated in this state, the incision or excision treatment can be completed (a step S33).

On the other hand, when the operator has given a treatment to a tissue including a blood vessel (e.g., the first bone 12 or its surrounding tissue) and this tissue has had a hemorrhage, the operator can give a hemostatic treatment as required. The hemostatic treatment will now be described hereinafter with reference to a flowchart shown in FIG. 12. In case of giving the hemostatic treatment, the operator arranges an end face 28A of the sheath 28 shown in FIG. 6 to abut on the tissue having the hemorrhage (e.g., the first bone 12 or its surrounding tissue). In this state, when the operator operates the second button 46, the third energy is supplied from the end face 28A of the sheath 28 (a step S31'). Since the third energy is constituted of the high-frequency current, the high-frequency current is supplied from the end face 28A of the sheath 28, and the tissue having the hemorrhage can be cauterized.

The high-frequency current supplied from the end face 28A of the sheath 28 is recovered by the probe 33 through the liquid having electrical conductivity filling the bone and the joint cavity 18. The high-frequency current recovered by the probe 33 is returned to the high-frequency energy output section 47. In such a hemostatic treatment, the control section 48 can display various kinds of statuses, e.g., an output state of the ultrasonic energy of the treatment tool 14 and an output state of the high-frequency energy of the treatment tool 14, the estimated time required for the perfusate 21 to reach the threshold value, and the remaining time before the estimated time in the display section 24 (a step S32'). When the surgery is terminated in a state where the temperature of the perfusate 21 does not exceed the threshold value, the hemostatic treatment can be completed as it is (a step S33').

When the supply of the third energy is continued during the hemostatic treatment, the high-frequency current flows through the perfusate 21, and the temperature of the perfusate 21 increases. Further, when the temperature of the perfusate 21 reaches the threshold value or more, the control section 48 switches the energy to be supplied to the probe 33 from the third energy to the fourth energy (a step S34', a step S35'). Since the fourth energy is the ultrasonic vibration provided by reducing the amplitude to be smaller than the normal amplitude without flowing the high-frequency current, the temperature of the perfusate 21 does not keep increasing any longer. In a state after the control section 48 has switched the third energy to the fourth energy, the control section 48 can display various kinds of statuses, e.g., an output state of the ultrasonic energy of the treatment tool 14, an output state of the high-frequency energy of the treatment tool 14 (a state where output of the high-frequency energy is stopped), and others in the display section 24 (a step S36'). When the surgery is terminated in a state where the energy has been switched to the fourth energy, the hemostatic treatment can be completed as it is (a step S37').

Furthermore, during continuation of the hemostatic treatment in the state where the energy has been switched to the fourth energy, when the temperature of the perfusate 21 falls below the safe temperature which is, e.g., 5° C. to 10° C. lower than the threshold value, the control section 48 switches the energy to be supplied to the probe 33 from the fourth energy to the third energy (steps S38' and S31'). In a state after the control section 48 has switched the fourth energy to the third energy, the control section 48 can display various kinds of statuses, e.g., an output state of the ultrasonic energy of the treatment tool 14 and an output state of the high-frequency energy of the treatment tool 14, the estimated time required for the perfusate 21 to reach the threshold value, and the remaining time before the estimated time in the display section 24 (the step S32'). When the hemostatic treatment is terminated in this state, the hemostatic treatment can be finished (the step S33').

After the end of the hemostatic treatment, the operator can restart the incision/removal of an unfavorable part of the first bone 12 and its surrounding biotissue by using the treatment section 44 of the probe 33 on the basis of the flowchart of FIG. 3 as required. As described above, in this embodiment, the operator can perform the incision/excision treatment of a biotissue, e.g., a bone and the hemostatic treatment in case of a hemorrhage by using the same treatment tool 14. Moreover, in this embodiment, since the control to switch the types of energy is performed when the temperature of perfusate 21 increases, a biotissue present around a treatment target region is not adversely affected by heat.

The control section 48 displays the estimation information estimated from the measurement temperature in the display section 24. According to this configuration, the operator can determine a procedure of the surgery on the basis of the estimation information, and the operator's convenience can be improved.

It is to be noted that, in this embodiment, when a temperature of the perfusate 21 is equal to or higher than the threshold value, the control section 48 automatically switches between the first energy and the second energy and switches between the third energy and the fourth energy, but the operator may manually perform such switching operations on the basis of a measurement temperature displayed in the display section 24 or display of a warning showing that the perfusate 21 has a high temperature.

Modification of Third Embodiment

A modification of the joint surgical system 11 according to the third embodiment will now be described. Although a first modification is different from the third embodiment in that the sensor 22 (the measurement section) is not provided, but other structures are the same as those in the third embodiment. Thus, parts different from the third embodiment will be mainly described, and an illustration or a description on parts equal to the third embodiment will be omitted. The joint surgical system 11 according to the modification of the third embodiment has the same appearance as that of the joint surgical system 11 according to the modification of the second embodiment shown in FIG. 9.

The power supply unit 15 has the ultrasonic energy output section 41 (the ultrasonic output section), the high-frequency energy output section 47 (the high-frequency output section), and the control section 48 which controls these sections. The control section 48 can control supply of the ultrasonic energy from the ultrasonic energy output section 41 and supply of the high-frequency energy from the high-frequency energy output section 47.

When the operator operates the first button 45, the control section 48 can output from the treatment tool 14 (the probe 33, the sheath 28) either the first energy suitable for incision or excision of a bone tissue (a biotissue) or the second energy used as alternative energy of the first energy. Likewise, when the operator operates the second button 46, it can output from the treatment section 14 (the probe 33, the sheath 28) either the third energy suitable for coagulation or hemostasis of the bone tissue (the biotissue) or the fourth energy used as alternative energy of the third energy. Compositions of the first energy to the fourth energy are the same as those in the third embodiment.

The control section 48 has an algorithm (software) that enables estimating a temperature of the perfusate 21, which has increased beyond a room temperature, on the basis of a supply time for which a high-frequency current is supplied to the perfusate 21. According to this algorithm, a quantity of heat to be generated can be calculated from the supply time of the high-frequency energy, and a current temperature of the perfusate 21 can be calculated as an estimated temperature from specific heat of the perfusate 21, a liquid volume of the perfusate 21, a room temperature, and others.

Further, the control section 48 can calculate an estimated time required for a perfusate 21 to eventually reach a threshold value from a room temperature, a total supply time of the high-frequency current, specific heat of the perfusate 21, a liquid volume of the perfusate 21, a current temperature of the perfusate 21, and others. In a state before a treatment is started, a temperature of the perfusate 21 is a room temperature (r.t.). The control section 48 measures the room temperature, and calculates an inclination of a straight line from the total supply time of the high-frequency current, the specific heat of the perfusate 21, and the liquid volume of the perfusate 21, thereby calculating the estimated time required for the perfusate 21 to reach the threshold temperature. The control section 48 calculates the estimated time, and then displays a remaining time before the estimated time like "the high-frequency energy can be used for . . . minutes (or . . . seconds)". When the estimated time is elapsed, the control section 48 can display information indicative of switching to the ultrasonic vibration (the ultrasonic energy) in the display section 24. The estimated time and the remaining time are examples of estimation information displayed in the display section 24.

When the estimated temperature of the perfusate 21 is lower than a threshold value (a predetermined temperature) at the time of operating the first button 45, the control section 48 controls the ultrasonic energy output section 41 and the high-frequency energy output section 47 to output the first energy (the ultrasonic vibration, the high-frequency current) from the treatment tool 14. On the other hand, when the estimated temperature of the perfusate 21 is equal to or higher than the predetermined threshold value at the time of operating the first button 45, the control section 48 controls the ultrasonic energy output section 41 to output the second energy (the ultrasonic vibration) from the treatment tool 14. The threshold value is the same as that in the third embodiment.

When the estimated temperature of the perfusate 21 is lower than the threshold value at the time of operating the second button 46, the control section 48 controls the high-frequency energy output section 47 to output the third energy (the high-frequency current) from the treatment tool 14. On the other hand, when the estimated temperature of the perfusate 21 is equal to or higher than the predetermined threshold value at the time of operating the second button 46, the control section 48 controls the ultrasonic energy output section 41 to output the fourth energy (the ultrasonic vibration) from the treatment tool 14. The threshold value which serves as a criterion for judgment to output either the third energy or the fourth energy when the second button 46 is operated is the same as the above-described threshold value. The incision/excision treatment and the hemostatic treatment according to this modification are different from those of the third embodiment in that whether the temperature of the perfusate 21 is equal to or higher than the threshold value is determined on the basis of an estimated temperature calculated by the control section 48 rather than a temperature actually measured by the sensor 22, but other processes are carried out in the same procedure as that of the third embodiment.

Likewise, the incision/excision treatment and the hemostatic treatment according to this modification are different from those of the third embodiment in that whether the temperature of the perfusate 21 falls below the safe temperature is determined on the basis of an estimated temperature calculated by the control section 48 rather than a temperature actually measured by the sensor 22. That is, in this modification, the control section 48 holds information about how much a temperature lowers when a given liquid volume of the perfusate 21 is left for a given time. The control section 48 calculates a time required for the perfusate 21 which has reached a threshold value to lower to a safe temperature on the basis of a previously input liquid volume of the perfusate 21, and switches the second energy to the first energy or switches the fourth energy to the third energy after elapse of a time required to lower to the safe temperature.

According to this embodiment, the joint surgical system 11 includes an endoscope apparatus 17 which allows visual confirmation of the treatment target region and a display section 24 which displays video images taken by the endoscope apparatus 17, and the control section 48 displays the estimated temperature in the display section 24. According to this configuration, the operator can confirm the measurement temperature measured by the measurement section in the display section 24. Thus, since the operator can grasp a temperature of the perfusate 21 and then conduct surgery, the surgery can be safely carried out, and the operator's convenience can be improved.

It is to be noted that, in this embodiment, when an estimated temperature of the perfusate 21 is equal to or higher than the threshold value, the control section 48 automatically switches between the first energy and the second energy and switches between the third energy and the fourth energy, but the operator may manually perform such switching operations on the basis of the estimated temperature displayed in the display section 24 or display of a warning showing that the perfusate 21 has a high temperature.

According to this modification, the control section 48 displays estimation information estimated from the estimated temperature in the display section 24. According to this configuration, the operator can determine a procedure of the surgery on the basis of the estimation information, and the operator's convenience can be improved.

It is to be noted that, in this embodiment, when an estimated temperature of the perfusate 21 is equal to or higher than the threshold value, the control section 48 automatically switches between the first energy and the second energy and switches between the third energy and the fourth energy, but the operator may manually perform such switching operations on the basis of the estimated temperature displayed in the display section 24 or display of a warning showing that the perfusate 21 has a high temperature.

Fourth Embodiment

A joint surgical system 11 according to a fourth embodiment will now be described with reference to FIG. 13. The joint surgical system 11 according to the fourth embodiment is different from that of the third embodiment in that a sensor 22 is provided at a distal end portion of a cannula 51, but other parts are the same as those of the third embodiment. Thus, parts different from the third embodiment will be mainly described, and an illustration or a description on parts equal to the third embodiment will be omitted.

The joint surgical system 11 includes a treatment tool 14, a power supply unit 15 which operates the treatment tool 14, an endoscope apparatus 17 including an arthroscope 16, a tubular cannula 51 (a tubular portion) which is arranged to pierce through a patient's skin to guide the treatment tool 14 to a joint cavity 18, and a sensor 22 which can measure a temperature of a perfusate 21 which fills the joint cavity 18 at the time of surgery.

The sensor 22 (a measurement section) is constituted of a generally available temperature sensor such as a thermocouple. The sensor 22 is provided on a distal end portion of the cannula 51 at a position where it comes into contact with the perfusate 21. The sensor 22 can measure a temperature of the perfusate 21 in the joint cavity 18. The sensor 22 may be provided at a position of an end face of a cylinder of the cannula 51 as shown in FIG. 13, may be provided on an inner peripheral surface of the cylinder of the cannula 51 near the end face, or may be provided on an outer peripheral surface of the cannula 51 near the end face.

An arthroscopic surgery method using the joint surgical system 11 according to this embodiment is the same as that of the third embodiment.

According to this embodiment, the joint surgical system 11 includes the tubular portion which guides the treatment tool 14 into the joint cavity 18, and the measurement section is provided at a position on the tubular portion where it comes into contact with the liquid. According to this configuration, since the measurement section is provided on the tubular portion different from the treatment tool 14, the measurement section does not obstruct an operation during a surgery, and a patient's convenience can be improved.

The present invention is not restricted to the foregoing embodiments, and it can be appropriately modified without departing from a gist thereof. Further, as a matter of course, the joint surgical systems according to the foregoing embodiments can be combined to constitute one joint surgical system.

REFERENCE SIGNS LIST

11 . . . joint surgical system, 12 . . . first bone, 14 . . . treatment tool, 17 . . . endoscope apparatus, 18 . . . joint cavity, 21 . . . perfusate, 22 . . . sensor, 24 . . . display section, 41 . . . ultrasonic energy output section, 47 . . . high-frequency energy output section, 48 . . . control section, and 51 . . . cannula.

What is claimed is:

1. A joint surgical system comprising:
a treatment tool configured to give a high-frequency treatment using a high-frequency current and an ultrasonic treatment using ultrasonic vibration to treat a treatment target region in a joint cavity filled with a liquid having electrical conductivity;
a high-frequency output circuit which is configured to output high-frequency energy for the high-frequency treatment to the treatment tool;
an ultrasonic output circuit which is configured to output ultrasonic energy for the ultrasonic treatment to the treatment tool;
a sensor which is configured to measure a temperature of the liquid; and
a controller which is configured to control:
the high-frequency output circuit to stop output of the high-frequency energy, and
the ultrasonic output circuit to continue output of the ultrasonic energy when a measurement temperature measured by the sensor is equal to or higher than a predetermined temperature,
wherein, when the measurement temperature is equal to or higher than the predetermined temperature, the controller is configured to control the ultrasonic output circuit so that the ultrasonic energy decreases to be lower than that in a state where the measurement temperature is lower than the predetermined temperature.

2. The system according to claim 1, wherein, when the measurement temperature is equal to or higher than the predetermined temperature, the controller is configured to control the ultrasonic output circuit so that the ultrasonic energy increases to be higher than that in a state where the measurement temperature is lower than the predetermined temperature.

3. The system according to claim 1, further comprising:
an endoscope apparatus which enables visually confirming the treatment target region; and
a display section which is configured to display video images taken by the endoscope apparatus,
wherein the controller is configured to display the measurement temperature in the display section.

4. The system according to claim 3, wherein the controller is configured to display estimation information estimated from the measurement temperature in the display section.

5. The system according to claim 1, wherein the sensor is provided at a position on the treatment tool where it comes into contact with the liquid.

6. The system according to claim 1, further comprising a tubular portion which is configured to guide the treatment tool into the joint cavity,
wherein the sensor is provided at a position on the tubular portion where it comes into contact with the liquid.

7. A joint surgical system comprising:
a treatment tool configured to give a high-frequency treatment and an ultrasonic treatment to treat a treatment target region in a joint cavity filled with a liquid having electrical conductivity;
a high-frequency output circuit which is configured to output high-frequency energy for the high-frequency treatment to the treatment tool;
an ultrasonic output circuit which is configured to output ultrasonic energy for the ultrasonic treatment to the treatment tool; and
a controller which is configured to:
estimate a temperature of the liquid, and
control the high-frequency output circuit to stop output of the high-frequency energy, and also control the ultrasonic output circuit to continue output of the ultrasonic energy when an estimated temperature provided by the estimation is equal to or higher than a predetermined temperature.

8. The system according to claim 7, wherein, when the estimated temperature is equal to or higher than the predetermined temperature, the controller is configured to control the ultrasonic output circuit so that the ultrasonic energy increases to be higher than that in a state where the estimated temperature is lower than the predetermined temperature.

9. The system according to claim 7, wherein, when the estimated temperature is equal to or higher than the predetermined temperature, the controller is configured to control the ultrasonic output circuit so that the ultrasonic energy decreases to be lower than that in a state where the estimated temperature is lower than the predetermined temperature.

10. The system according to claim 7, further comprising:
an endoscope apparatus which enables visually confirming the treatment target region; and
a display section which is configured to display video images taken by the endoscope apparatus,
wherein the controller is configured to display the estimated temperature in the display section.

11. The system according to claim 10, wherein the controller is configured to display estimation information estimated from the estimated temperature in the display section.

* * * * *